United States Patent
Persson et al.

(10) Patent No.: US 6,538,114 B1
(45) Date of Patent: *Mar. 25, 2003

(54) HUMAN MONOCLONAL ANTIBODIES SPECIFIC FOR HEPATITIS C VIRUS (HCV) E2 ANTIGEN

(75) Inventors: Mats Axel Atterdag Persson, Stockholm (SE); Tobias Erik Allander, Stockholm (SE)

(73) Assignee: Karolina Innovations AB, Stockholm (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/635,109

(22) Filed: Apr. 19, 1996

(51) Int. Cl.[7] .......................... C12P 21/08; A61K 39/42
(52) U.S. Cl. ................. 530/388.3; 530/388.1; 424/133.1; 424/130.1; 424/139.1; 424/141.1; 424/147.1; 424/149.1; 435/5; 435/7.1; 435/69.1; 435/240.2
(58) Field of Search .......................... 435/5, 7, 69.1, 435/240.2, 424, 530; 530/388.3; 424/133.1, 130.1, 139.1, 141.1, 147.1, 149.1, 800, 809

(56) References Cited

U.S. PATENT DOCUMENTS

| | | |
|---|---|---|
| 5,308,750 A | 5/1994 | Mehta et al. |
| 5,919,454 A * | 7/1999 | Brechot et al. .......... 424/161.1 |

FOREIGN PATENT DOCUMENTS

| | | |
|---|---|---|
| EP | 0 447 984 A1 | 9/1991 |
| WO | WO 92/20791 | 11/1992 |
| WO | WO 93/06213 | 4/1993 |

OTHER PUBLICATIONS

Wong et al. 1995 J Investigative Medicine 43 (2) Supplement 2 397A, Apr. 1, 1995.*
Farci et al. 1992 Science vol. 258 pp. 135–140.*
Barbas III et al., "Assembly of combinatorial antibody libraries on phage surfaces: The gene III site," *Proc. Natl. Acad. Sci.* USA (88):7978–7982 (1991).
Barbas III et al., "Synthetic human antibodies: Selecting and evolving functional proteins," *Methods: A Companion to Methods in Enzymology* (8):94–103 (1995).
Burton et al., "A large array of human monoclonal antibodies to type 1 human immunodeficiency virus from combinmatorial libraries of asymtomatic seropositive individuals," *Proc. Natl. Acad. Sci. USA* (88):10134–10137 (1991).
Chanock et al., "Human monoclonal antibody fab fragments cloned from combinatorial libraries: potential usefulness in prevention and/or treatment of Major human viral diseases," *Infectious Agents and Disease* 2(3):118–131 (1993).
Persson et al., "Generation of diverse high–affinity human monoclonal antibodies by repertoire cloning," *Proc. Natl. Acad. Sci. USA* (88) 2432–2436 (1991).
Rosa et al., "A quantitative test to estimate neutralizing antibodies to the hepatitis C virus; Cytofluorimetric assessment of envelope glycoprotein 2 binding to target cells," *Proc. Natl. Acad. Sci. USA* (93):1759–1763 (1996).
Samuelsson et al., "Chimeric macaque/human fab molecules neutralize simian immunodeficiency virus," *Virology* (207):495–502 (1995).

* cited by examiner

Primary Examiner—Mary K. Zeman
(74) Attorney, Agent, or Firm—Robins & Pasternak LLP

(57) ABSTRACT

The present invention relates to compositions derived from immunoglobulin molecules specific for the hepatitis C virus (HCV). More particularly, the invention is related to molecules which are capable of specifically binding with HCV E2 antigen. The molecules are useful in specific binding assays, affinity purification schemes and pharmaceutical compositions for the prevention and treatment of HCV infection in mammalian subjects. The invention thus relates to novel human monoclonal antibodies specific for HCV E2 antigen, fragments of such monoclonal antibodies, polypeptides having structure and function substantially homologous to antigen-binding sites obtained from such monoclonal antibodies, nucleic acid molecules encoding those polypeptides, and expression vectors comprising the nucleic acid molecules.

46 Claims, 9 Drawing Sheets

FIG. 1A (1:5, HEAVY CHAIN) [SEQ ID NO.: 1]

EVQLLEQSGA EVRKPGSSVK VSCKASGGTF SGHYIWVRQ APGQGLEWMG ESIPIFGSAN YAQNYAQKF DRVSIIADES TSTSFIELSN LRSDDTAVYY CARDPPRYCS AGRCYTGFFQ QWGQGTLVTV SS

CDR1         CDR2                    CDR3

FIG. 1B (1:7, HEAVY CHAIN) [SEQ ID NO.: 2]

EVQLLEQSGA EVKKPGSSVK VSCQVFGDTF SRKTIQWLRQ APGQGPEWMG NIIPVYNTPN YAQKFQGRLS ITADDSTSTA YMELSSLRSE DTAVYFCARV VIPNAIRHTM GYYEDYWGQG TLVTVSS

CDR1         CDR2                    CDR3

FIG. 1C (1:11, HEAVY CHAIN) [SEQ ID NO.: 3]

```
                     CDR1                          CDR2                                          CDR3
EVQLLEQSGA EVKKPGSSVK VSCKASGGTF SGHYISWVRQ APGQGLEWMG GSISFEGTSN SAQKFQGRVS ITADESASTA YMELSSLRSE DTAIYYCAKD PPRECSGGNC YPGHQQWGQ GTLVTVSS
```

FIG. 1D (L3, HEAVY CHAIN) [SEQ ID NO.: 4]

```
                     CDR1                          CDR2                                          CDR3
EVQLLESGGG VVQPGRSLRL SCAASGFTFK TYGMHWVRQA PGKGLEWVAG ISFDGSNQYY ADSVKGRFIV SRDNSRDTVF LQMSSLRLED TAVYYCATEG SPEGSIKGRY YLENWGQGTL VTVSS
```

FIG. 2A (1:5, HEAVY CHAIN) [SEQ ID NO.: 5]

```
         CDR1                              CDR 2                                           CDR3
AELTQSPGTL SLSPGERATL SCRASQSVSS NYLAWYQQRP GQAPRLLIYG ASSRATGIPD RFSGSGSGTD FTLTISRLEP EDFAVYYCQL YGNSRWTFGQ GTKVEIK
```

FIG. 2B (1:7, HEAVY CHAIN) [SEQ ID NO.: 6]

```
         CDR 1                             CDR 2                                          CDR3
AELTQSPATL SLSPGERATL SCRASQSVNK YLAWYQQKPG QAPRLLIYDA SNRATGIPAR FSGSGSGTDF TLTISNLEPE DFAVYYCQQR SDWVTFGGGT KVEIK
```

FIG. 2C (1:11, HEAVY CHAIN) [SEQ ID NO.: 7]

```
           CDR1                           CDR 2                                    CDR3
AELTQSPGTL SLSPGERATL SCGASQSVRS NYLAWYQQKP GQAPRLLIYG VSSRATGIPD RFSGSGSGTD FLTISRLEP EDFAVYYCQQ YGSSPRTFGQ GTKLEIK
```

FIG. 2D (L3, HEAVY CHAIN) [SEQ ID NO.: 8]

```
           CDR 1                          CDR 2                                    CDR3
AELTQSPATL SVSPGERASL SCRASQSVGN NLAWYQQKPG QAPRLLIYGG NTRAIGTPDR FSGSGSGTEF TLTISSLQSE DFAVYFCQHY STWPLTFGGG TKVEFK
```

FIG. 3A (1:5, HEAVY CHAIN) [SEQ ID NO.: 9]

GAGCTCAGGC AGTCTCCAGG CACCCTGTCT TTGTCTCCAG GGGAAAGAGC CACCCTCTCC TGCAGGGCCA
GTCAGAGTGT TAGCAGCAAT TACTTAGCCT GGTACCAGCA GAGACCTGGC CAGGCTCCCA GGCTCCTCAT
CTATGGTGCA TCCAGCAGGG CCACTGGCAT CCCAGACAGG TTCAGTGGCA GTGGGTCTGG GACAGACTTC
ACTCTCACCA TCAGCAGACT GGAGCCTGAA GATTTTGCAG TGTATTACTG TCAGCTTTAT GGTAACTCAC
GTTGGACGTT CGGCCAAGGG ACCAAGGTGG AGATCAAA

FIG. 3B (1:7, HEAVY CHAIN) [SEQ ID NO.: 10]

GAGCTCACTC AGTCTCCAGC CACCCTGTCT TTGTCTCCAG GGGAAAGAGC CACCCTCTCC TGCAGGGCCA
GTCAGAGTGT TAACAAGTAC TTAGCCTGGT ACCAACAGAA ACCTGGCCAG GCTCCCAGGC TCCTCATCTA
TGATGCATCC AACAGGGCCA CTGGCATCCC AGCCAGGTTC AGTGGCAGTG GGTCTGGGAC AGACTTCACT
CTCACCATCA GCAACCTAGA GCCTGAAGAT TTTGCAGTTT ATTACTGTCA GCAGGGTAGC GACTGGGTCA
CTTTCGGCGG AGGGACCAAG GTGGAGATCA AA

FIG. 3C (1:11, HEAVY CHAIN) [SEQ ID NO.: 11]

GAGCTCACGC AGTCTCCAGG CACCCTGTCT TTGTCTCCAG GGGAAAGAGC CACCCTCTCC TGCGGGCCA
GTCAGAGTGT TAGGAGCAAC TACTTAGCCT GGTACCAGCA AAAACCTGGC CAGGCTCCCA GGCTCCTCAT
CTATGGTGTA TCCAGCAGGG CCACTGGCAT CCCAGACAGG TTCAGTGGCA GTGGGTCTGG GACAGACTTC
ACTCTCACCA TCAGCAGACT GGAGCCTGAA GATTTTGCAG TGTATTACTG TCAGCAGTAT GGTAGCTCAC
CTCGGACTTT TGGCCAGGGG ACCAAGTTGG AGATCAAA

FIG. 3D (L3, HEAVY CHAIN) [SEQ ID NO.: 12]

GAGCTCACGC AGTCTCCAGC CACCCTGTCT GTGTCTCCAG GGGAAAGAGC CTCCCTCTCC TGCAGGGCCA
GTCAGAGTGT CGGTAACAAT TTAGCTTGGT ATCAGCAGAA ACCTGGCCAG GCTCCCAGGC TCCTCATTTA
TGGTGGAAAC ACCAGAGCCA CTGGTACCCC AGACAGGTTC AGTGGCAGTG GGTCTGGGAC AGAATTCACT
CTCACCATCA GCAGCCTGCA GTCTGAGGAC TTTGCAGTTT ATTTCTGTCA ACACTATAGT ACCTGGCCGC
TCACTTTCGG CGGGGGGACC AAGGTCGAGT TCAAG

FIG. 4A (1:5, HEAVY CHAIN) [SEQ ID NO.: 13]

CTCGAGCAGT CTGGGGCTGA GGTGAGGAAG CCTGGGTCCT CGGTGAAGGT CTCCTGCAAG GCTTCTGGAG
GCACCTTCAG CGGCCATGTT ATCACCTGGG TGCGACAGGC CCCTGGACAA GGACTTGAGT GGATGGGAGA
GAGCATCCCT ATCTTTGGTT CCGCAAACTA CGCTCAAAAC TACGCTCAGA AATTCCGGGA CAGAGTCTCG
ATTATGCGGG ACGAATCCAC GAGCAGGTCG TTCATTGAGC TGAGCAACCT GAGATCTGAC GACACGGCCG
TCTACTACTG TGCGAGAGAC CCTCCAAGAT ATTGCAGTGC TGGTAGATGC TACCCGGGAT TCTTCCAGCA
GTGGGGCCAG GGCACCCTCG TCACCGTCTC CTCA

FIG. 4B (1:7, HEAVY CHAIN) [SEQ ID NO.: 14]

CTCGAGCAGT CTGGGGCTGA GGTGAAGAAG CCTGGGTCCT CGGTGAAGGT CTCCTGTCAG GTTTTTGGAG
ACACCTTCAG CAGATACACT ATTCAGTGGT TGCGACAGGC CCCTGGACAA GGGCCTGAGT GGATGGGAAA
TATCATCCCT GTCTATAATA CACCAAACTA CGCGCAGAAG TTTCAGGGCA GACTCTCGAT AACCGCCGAC
GATTCCACGA GCACAGCCTA CATGGAACTG AGTAGCCTCA GATCTGAGGA CACGGCCGTC TATTCTGTG
CGAGAGTCGT AATACCAAAT GCAATCCGGC ACACGATGGG ATATTACTTT GACTACTGGG GCCAGGGAAC
CCTGGTCACC GTCTCCTCA

FIG. 4C (1:11, HEAVY CHAIN) [SEQ ID NO.: 15]

CTCGAGCAGT CTGGGGCTGA GGTGAAGAAG CCTGGGTCCT CAGTGAAGGT CTCCTGCAAG GCTTCTGGAG
GCACCTTCAG CGGCCATGTT ATCAGCTGGG TGCGACAGGC CCCTGGACAA GGGCTTGAGT GGATGGGGGG
GAGTATCTCT TTCTTTGGCA CATCAAACTC CGCACAGAAG TTCCAGGGCA GAGTCTCGAT TACCGCGGAC
GAATCCGCGA GCACAGCCTA CATGGAGCTG AGTAGCCTGA GATCGGAGGA CACGGCCATC TATTACTGTG
CGAAAGACCC TCCAAGATTT TGTAGTGGTG GTAACTGCTA CCCGGGGTTC TTCCAGCAGT GGGGCCAGGG
CACCCTGGTC ACCGTCTCCT CA

FIG. 4D (L3, HEAVY CHAIN) [SEQ ID NO.: 16]

CTCGAGTCGG GGGGAGGCGT GGTCCAGCCT GGGAGGTCCC TGAGACTCTC CTGTGCAGCG TCTGGATTCA
CCTTCAAGAC GTATGGCATG CACTGGGTCC GCCAGGCTCC AGGCAAGGGG CTGGAGTGGG TGGCAGTTAT
TTCGTTTGAT GGAAGTAACC AATATTACGC AGACTCCGTG AAGGGCCGAT TCATCGTCTC CAGAGACAAT
TCCAGGGACA CGGTGTTTCT GCAGATGAGC AGCCTGAGAC TCGAGGACAC GGCTGTGTCT ATTACTGTGCA
CAGAGGGTTC TCCTTTGGC TCGATTAAGG GGGTTACTA CCTTGAAAAT TGGGGCCAGG GAACCCTGGT
CACCGTCTCC TCA

HUMAN MONOCLONAL ANTIBODIES SPECIFIC FOR HEPATITIS C VIRUS (HCV) E2 ANTIGEN

TECHNICAL FIELD

The present invention relates to compositions derived from immunoglobulin molecules specific for the hepatitis C virus (HCV). More particularly, the invention is related to recombinant human monoclonal antibodies which are capable of specifically binding with HCV E2 antigen.

BACKGROUND

Hepatitis C virus (HCV) infection occurs throughout the world and is the major cause of transfusion-associated hepatitis. There are an estimated 150,000 new cases of HCV infection each year in the United States. The seroprevalence of anti-HCV antibodies in blood donors from around the world has been shown to vary between 0.02 and 1.23%, with rates in some countries as high as about 19%. In addition to being the predominate cause of transfusion-induced hepatitis, HCV is also a common cause of hepatitis in individuals exposed to blood or blood products. Thus, recipients of blood or blood products, intravenous drug users, renal dialysis patients and needle-stick victims represent high-risk groups for HCV infection. Alter et al. (1993) *Infect Agents Dis* 2:155–166. Further, heterosexual transmission of HCV across the urogenital tract, and mother-to-baby transmission, has been well documented. Ohto et al. (1994) *N Engl J Med* 330:744–750. Other risk factors associated with HCV infection include familial or household contact with an HCV-infected individual and health-care employment with occupational exposure to blood and hemodialysis. Alter et al. (1990) *JAMA* 264:2231–2235. Chronic hepatitis develops in approximately 62% of infections. Alter et al. (1992) *N Engl J Med* 327:1899–1905.

Most of the serious liver disease associated with HCV results from the high propensity of the agent to cause chronic, persistent infection. Cirrhosis occurs in approximately 20% of chronic cases, of which 20 to 25% will result in liver failure. Another serious sequela associated with HCV infection is primary hepatocellular carcinoma.

The viral genomic sequence of HCV is known, as are methods for obtaining the sequence. See, e.g., International Publication Nos. WO 89/04669; WO 90/11089; and WO 90/14436. HCV has a 9.5 kb positive-sense, single-stranded RNA genome and is a member of the Flaviridae family of viruses. Currently, there are 6 distinct, but related genotypes of HCV which have been identified based on phylogenetic analyses (Simmonds et al., *J. Gen. Virol.* (1993) 74:2391–2399). The virus encodes a single polypeptide having more than 3000 amino acid residues (Choo et al. (1989) *Science* 244:359–362; Choo et al. (1991) *Proc. Natl. Acad. Sci. USA* 88:2451–2455; Han et al. (1991) *Proc. Natl. Acad. Sci. USA* 88:1711–1715). The polypeptide is processed co- and post-translationally into both structural and non-structural (NS) proteins.

In particular, there are three putative HCV structural proteins, consisting of the N-terminal nucleocapsid protein (termed "core") and two envelope glycoproteins, "E1" (also known as E) and "E2" (also known as E2/NS1). (See, Houghton et al. (1991) *Hepatology* 14:381–388, for a discussion of HCV proteins, including E1 and E2.) E1 is detected as a 32–35 kDa species and is converted into a single endo H-sensitive band of approximately 18 Kda. By contrast, E2 displays a complex pattern upon immunoprecipitation consistent with the generation of multiple species (Grakoui et al. (1993) *J. Virol.* 67:1385–1395; Tomei et al. (1993) *J. Virol.* 67:4017–4026). The HCV envelope glycoproteins E1 and E2 form a stable complex that is coimmunoprecipitable (Grakoui et al. (1993) *J. Virol.* 67:1385–1395; Lanford et al. (1993) *Virology* 197:225–235; Ralston et al. (1993) *J. Virol.* 67:6753–6761).

The only currently available treatment for chronic hepatitis C infection consists of α-interferon (α-IFN) therapy. However, long-term response to interferon therapy only occurs in 10% to 30% of treated individuals, and there is evidence that the different HCV strains vary greatly in their responsiveness to interferon therapy, with the type 1 viruses being the most refractive. Furthermore, flu-like side effects are commonly encountered with interferon therapy (occurring in approximately 60% to 80% of treated individuals), as well as other less common side effects such as nausea, depression, fatigue and thrombocytopenia. Interferon therapy is also not indicated for immunocompromised individuals. Accordingly, there exists a need for more effective therapeutic approaches in the treatment of chronic HCV infection. In this regard, some effect has been seen using ribivirin, or combination therapies with ursodiol and α-IFN.

In particular, the HCV E1 and E2 proteins are of considerable interest because recombinant vaccines based on those molecules have been shown to be protective against experimental challenge with HCV in primate studies. (Choo et al. (1994) *Proc. Natl. Acad. Sci. USA* 91:1294–1298). Hyperimmune globulin compositions of anti-HCV antibody molecules obtained from donor samples have been described for the treatment of HCV in infected individuals, and in the prevention of HCV infection in high-risk groups. European Patent Application Publication No. 447,984, published Sep. 25, 1991. Since these compositions are made from donor blood products, an inherent risk is associated with their use due to the possible presence of infectious against such as the Human Immunodeficiency Virus (HIV) and HCV. Accordingly, hyperimmune globulin preparations must be carefully screened, and all infectious agents inactivated prior to administration to human subjects.

It is known that the immune response to HCV in normal individuals includes both humoral and cell mediated components. Koziel et al. (1993) *J Virol* 67:7522–7532, Alter et al. (1989) *N Engl J Med* 321:1494–1500. Further, several reports have indicated that antibodies elicited to HCV may neutralize the infectivity of the virus. Shimizu et al. (1994) *J Virol* 68:1494–1500, Farci et al. (1994) *Proc Natl Acad Sci USA* 91:7792–7796. Such results provide hope that an effective antibody-based therapy can be developed. In this regard, the administration of a highly-reactive, neutralizing anti-HCV antibody preparation to an individual who is at risk of infection, or who has been recently exposed to the agent will provide immediate passive immunity to the individual. Such passive immunizations would likewise be expected to be successful in both normal and immunocompromised subjects. Preferably, the neutralizing antibodies would be broadly cross-reactive against different HCV strains, and would be monoclonal in order to control the effects of the use of the antibodies in vivo.

For a number of practical and economic reasons, murine monoclonal antibodies have been generally used in research and medicine. Murine antibodies can be raised against a wide variety of molecules, such as HCV antigens, and fused with a myeloma cell to yield hybridomas which can be grown in culture to produce monoclonal antibodies toward HCV antigens. Kohler et al. (1975) *Nature* 256:495–497. Although such monoclonal antibodies may have antigen binding specificities of significant therapeutic value, the use of such murine antibodies in the treatment of human disease has been limited since those molecules are immunogenic to the human immune system. Thus, murine monoclonals have been most commonly used in immunodiagnostics. In this regard, murine monoclonal antibodies to putative HCV E2 envelope polypeptides have been described for use in the detection of HCV in biological samples. U.S. Pat. No. 5,308,750 to Mehta et al.

Accordingly, there remains a need in the art to provide human monoclonal antibodies toward HCV E2 antigen, wherein the monoclonals are broadly cross-reactive with heterologous HCV isolates.

SUMMARY OF THE INVENTION

The present invention is based on the discovery of human monoclonal antibody molecules which exhibit immunological binding affinity for HCV E2 polypeptide antigen, and which are cross-reactive against different HCV strains. The monoclonal antibody molecules were obtained from a combinatorial library that was constructed from a nonimmunized HCV-infected source. The present molecules generally comprise a human antibody Fab molecule that exhibits immunological binding affinity for HCV E2 antigen.

Accordingly, in one embodiment, the invention is directed to a recombinant human monoclonal antibody that exhibits immunological binding affinity for HCV E2 antigen, wherein the monoclonal antibody includes amino acid sequences that are homologous to the binding portion of a human antibody Fab molecule obtained from a combinatorial antibody library. The recombinant monoclonal antibody molecule can be in the form of a substantially whole immunoglobulin molecule, or can be in the form of a soluble Fab molecule, an Fv fragment, or an sFv molecule, wherein each molecule at least contains amino acid sequences that are homologous to the binding portion of a human antibody Fab molecule.

In another embodiment, the invention is directed to an isolated nucleic acid molecule which contains a polynucleotide coding sequence for a polypeptide that is homologous to the binding portion of a heavy or light chain variable region ($V_H$ or $V_L$) of a human Fab molecule which exhibits immunological binding affinity for HCV E2 antigen. In a related embodiment, the invention is directed to an isolated nucleic acid molecule which contains polynucleotide coding sequences for a first polypeptide and polynucleotide coding sequences for a second polypeptide, wherein the first polypeptide is homologous to the binding portion of a heavy chain variable region ($V_H$) of a human Fab molecule which exhibits immunological binding affinity for HCV E2 antigen, and the second polypeptide is homologous to the binding portion of a light chain variable region ($V_L$) of a human Fab molecule which exhibits immunological binding affinity for the HCV E2 antigen.

In other embodiments, the invention pertains to expression vectors comprising the nucleic acid molecules above operably linked to control sequences that direct the transcription of the polynucleotide coding sequences when the vector is present in a host cell or under suitable conditions for the transcription and translation of the polynucleotide coding sequences. Yet further embodiments of the invention pertain to host cells transformed with the vectors of the invention, and methods for producing recombinant polypeptides using the transformed host cells.

In another embodiment, the invention is directed to vaccine compositions comprising the recombinant monoclonal antibody molecules of the invention. Still further embodiments relate to methods of using the vaccine compositions, wherein the vaccines are used to provide an antibody titer to HCV in a mammalian subject, and/or used to provide passive immunity against HCV infection in a vaccinated subject. In related embodiments, the vaccine compositions are used in combination with known anti-HCV therapeutics.

In still further embodiments, the recombinant monoclonal antibody molecules of the invention are used to provide binding complexes which are labeled with a detectable moiety. The labeled binding complexes are used in related embodiments of the invention, such as in specific binding assay methods, for detecting the presence of HCV particles in samples suspected of containing HCV and in specific binding assays for monitoring the progress of anti-HCV treatment of HCV-infected subjects.

These and other embodiments of the present invention will readily occur to those of ordinary skill in the art in view of the disclosure herein.

BRIEF DESCRIPTION OF THE FIGURES

FIGS. 1A–1D depict the deduced γ1 heavy chain amino acid sequences of the Fab molecule clones 1:5 [SEQ ID NO.: 1], 1:7 [SEQ ID NO.: 2], 1:11 [SEQ ID NO.: 3], and L3 [SEQ ID NO.: 4], respectively. The CDR regions of each heavy chain have been identified in the Figures as "CDR1," "CDR2" and "CDR3."

FIGS. 2A–2D depict the deduced κ light chain amino acid sequences of the Fab molecule clones 1:5 [SEQ ID NO.: 5], 1:7 [SEQ ID NO.: 6], 1:11 [SEQ ID NO.: 7], and L3 [SEQ ID NO.: 8], respectively. The CDR regions (CDR1, CDR2 and CDR3) of each light chain have also been identified as noted in regard to FIGS. 1A–1D above.

FIGS. 3A–3D depict the κ light chain nucleic acid sequences of the Fab molecule clones 1:5 [SEQ ID NO.: 9], 1:7 [SEQ ID NO.: 10], 1:11 [SEQ ID NO.: 11], and L3 [SEQ ID NO.: 12], respectively.

FIGS. 4A–4D depict the γ1 heavy chain nucleic acid sequences of the Fab molecule clones 1:5 [SEQ ID NO.: 13], 1:7 [SEQ ID NO.: 14], 1:11 [SEQ ID NO.: 15], and L3 [SEQ ID NO.: 16], respectively.

DETAILED DESCRIPTION OF THE INVENTION

Figure 5:
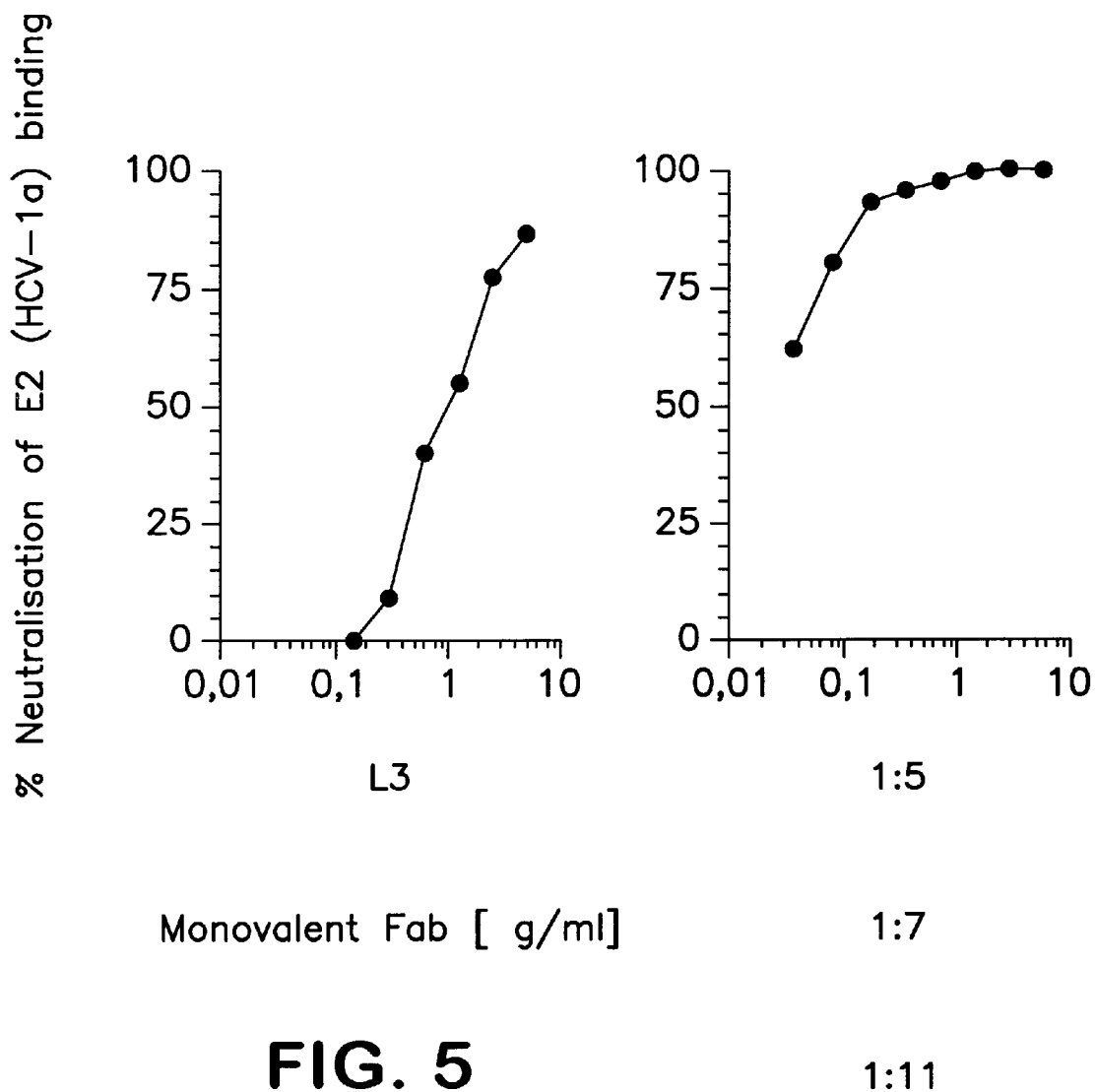
FIG. 5 depicts the results of a neutralization assay conducted as described in Example 12 wherein the ability of Fab molecules expressed from the Fab molecule clones 1:5, 1:7, 1:11 and L3 to block the binding of HCV E2 polypeptide to target cells was assessed.

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. *Molecular Cloning: A Laboratory Manual* (2nd Edition, 1989); *DNA Cloning: A Practical Approach,* vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984); *Fundamental Virology,* 2nd Edition, vol. I & II (B. N. Fields and D. M. Knipe, eds.)

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

As used herein, the terms "hepatitis C virus," or "HCV" describe the virus in a generic manner, and as such the terms are not limiting to any particular HCV viral sequence or isolate. In this regard, there are 6 distinct genotypes of HCV with 11 distinct subtypes which have been identified based on phylogenetic analyses (Houghton, M. (1996) "Hepatitis C Viruses," *Fields Virology*, 3d Edition, Fields et al. eds., Lippincott-Raven Publishers, Philadelphia Pa.; Simmonds et al., *J. Gen. Virol.* (1993) 74:2391–2399). Further, comparison of genomic nucleotide sequences from different HCV isolates around the world establish that HCV is highly heterogenous, with a range of sequence diversity among 74 isolates. Thus, the terms "hepatitis C virus," and "HCV" as used herein will generically encompass all such isolates.

The terms "an antigen derived from an E1 polypeptide," an "E1 polypeptide antigen" and "an HCV E1 antigen" are used interchangeably herein and encompass molecules from an HCV E1 region. The term "polypeptide," as used herein, refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. E1 polypeptides antigens can be physically derived from the HCV E1 region or produced recombinantly or synthetically, based on the known sequence. The mature E1 region of HCV1 begins at approximately amino acid 192 of the polyprotein and continues to approximately amino acid 383.

A polypeptide or amino acid sequence "derived from" a designated HCV region refers to a polypeptide having an amino acid sequence identical to that of a polypeptide encoded in the sequence, or a portion thereof wherein the portion consists of at least 3–5 amino acids, preferably at least 4–7 amino acids, more preferably at least 8–10 amino acids, and even more preferably at least 11–15 amino acids, or which is immunologically identifiable with a polypeptide encoded in the sequence. This terminology also includes a polypeptide expressed from a designated HCV region.

The terms "an antigen derived from an E2 polypeptide," an "E2 polypeptide antigen" and "an HCV E2 antigen" are used interchangeably herein and encompass molecules from an HCV E2 region. Such molecules can be physically derived from the region or produced recombinantly or synthetically, based on the known sequence. The mature E2 region of HCV1 is believed to begin at approximately amino acid 384–385.

For purposes of the present invention, HCV E1 and E2 polypeptides are defined with respect to the amino acid number of the polyprotein encoded by the genome of HCV1, with the initiator methionine being designated position 1. However, it should be noted that an antigen from an "E1 polypeptide" or an "E2 polypeptide" is not limited to polypeptides having an exact HCV1 sequence. Indeed, the HCV genome is in a state of constant flux and contains several variable domains which exhibit relatively high degrees of variability between isolates. It is readily apparent that the terms encompass antigens from E1 and E2 polypeptides from any of the various HCV isolates including isolates having any of the 6 genotypes of HCV described in Simmonds et al., *J Gen Virol* (1993) 74:2391–2399). In this regard, the corresponding E1 or E2 regions in a heterologous HCV isolate can be readily determined by aligning sequences from the two isolates in a manner that brings the sequences into maximum alignment. This can be performed with any of a number of computer software packages, such as ALIGN 1.0, available from the University of Virginia, Department of Biochemistry (Attn: Dr. William R. Pearson). See, Pearson et al., *Proc Natl Acad Sci USA* (1988) 85:2444–2448.

Additionally, the terms "E1 polypeptide antigen" and "E2 polypeptide antigen" encompass polypeptides which include modifications to the native sequence, such as internal deletions, additions and substitutions (generally conservative in nature). These modifications may be deliberate, as through site-directed mutagenesis, or may be accidental, such as through naturally occurring mutational events.

An "E1/E2 complex" refers to a complex of the E1 and E2 polypeptides described above. The mode of association of E1 and E2 in such a complex is immaterial. Indeed, such a complex may form spontaneously simply by mixing E1 and E2 polypeptides which have been produced individually. Similarly, when co-expressed and secreted, E1 and E2 polypeptides can form a complex spontaneously in the media. Formation of an "E1/E2 complex" is readily determined using standard protein detection techniques such as polyacrylamide gel electrophoresis and immunological techniques such as immunoprecipitation.

The term "antibody" encompasses monoclonal antibody preparations, as well as preparations including hybrid antibodies, altered antibodies, F(ab')$_2$ fragments, F(ab) molecules, Fv fragments, single domain antibodies, chimeric antibodies and functional fragments thereof which exhibit immunological binding properties of the parent antibody molecule.

As used herein, the term "monoclonal antibody" refers to an antibody composition having a homogeneous antibody population. The term is not limited by the manner in which it is made. The term encompasses whole immunoglobulin molecules, as well as Fab molecules, F(ab')$_2$ fragments, Fv fragments, and other molecules that exhibit immunological binding properties of the parent monoclonal antibody molecule. The term "recombinant monoclonal antibody" is defined herein as a monoclonal antibody that has been produced by expression of a recombinant polynucleotide.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev Biochem* 59:439–473.

A number of therapeutically useful molecules are known in the art which comprise antigen-binding sites that are capable of exhibiting immunological binding properties of an antibody molecule. One such molecule is a Fab molecule which comprises a heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$:$V_L$ heterodimer including an antigen-binding site which retains much of the antigen recognition and binding capabilities of the native antibody molecule. Inbar et al. (1972) *Proc. Nat. Acad. Sci. USA* 69:2659–2662; Hochman et al. (1976) *Biochem* 15:2706–2710; and Ehrlich et al. (1980) *Biochem* 19:4091–4096.

A polypeptide molecule, or amino acid sequence "derived from" a designated Fab molecule or Fab nucleic acid sequence refers to a polypeptide having an amino acid sequence identical to that of a Fab polypeptide encoded in the sequence, or a portion thereof wherein the portion consists of at least 3–5 amino acids, preferably at least 4–7 amino acids, more preferably at least 8–10 amino acids, and even more preferably at least 11–15 amino acids.

A single chain Fv ("sFv") polypeptide molecule is a covalently linked $V_H$:$V_L$ heterodimer which is expressed from a gene fusion including $V_H$- and $V_L$-encoding genes linked by a peptide-encoding linker. Huston et al. (1988) *Proc Nat Acad Sci USA* 85(16):5879–5883. A number of methods have been described to discern chemical structures for converting the naturally aggregated, but chemically separated, light and heavy polypeptide chains from an antibody V region into an Sfv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3," respectively. An antigen-binding site, therefore, includes six CDRs, comprising the CDR set from each of a heavy and a light chain V region.

As used herein, the term "FR set" refers to the four flanking amino acid sequences which frame the CDRs of a CDR set of a heavy or light chain V region. Some FR residues may contact bound antigen; however, Frs are primarily responsible for folding the V region into the antigen-binding site, particularly the FR residues directly adjacent to the CDRs.

By "purified" and "isolated" is meant, when referring to a polypeptide or nucleotide sequence, that the indicated molecule is present in the substantial absence of other biological macromolecules of the same type. The terms "purified" and "isolated" as used herein preferably mean at least 75% by weight, more preferably at least 85% by weight, more preferably still at least 95% by weight, and most preferably at least 98% by weight, of biological macromolecules of the same type are present. An "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition. Thus, for example, an isolated nucleic acid molecule which encodes the binding portion of a particular heavy chain variable region consists essentially of the nucleotide coding sequence for the subject binding portion (e.g., the CDR set interposed between the FR set).

"Homology" refers to the percent of identity between two polynucleotide or polypeptide moieties. The correspondence between two or more sequences can be determined by techniques known in the art. For example, homology can be determined by a direct comparison of the sequence information between two polypeptide molecules. Alternatively, homology can be determined by hybridization of polynucleotides under conditions which form stable duplexes between homologous regions (for example, those which would be used prior to $S_1$ digestion), followed by digestion with single-stranded specific nuclease(s), followed by size determination of the digested fragments. Two DNA or polypeptide sequences are "substantially homologous" when at least about 60% (preferably at least about 80%, and most preferably at least about 90%) of the nucleotides or amino acids match over a defined length of the molecule.

The terms "recombinant DNA molecule," or "recombinant nucleic acid molecule" are used herein to refer to a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature. Thus, the term encompasses "synthetically derived" nucleic acid molecules.

The term "nucleic acid molecule" as used herein refers to a polymeric form of nucleotides of any length, either ribonucleotides or deoxyribonucleotides. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

A "coding sequence" is a nucleic acid molecule which is translated into a polypeptide, usually via mRNA, when placed under the control of appropriate regulatory sequences. The boundaries of the coding sequence may be determined by a translation start codon at the 5'-terminus and a translation stop codon at the 3'-terminus. A coding sequence can include, but is not limited to, CDNA, and recombinant nucleotide sequences.

"Control sequence" refers to nucleic acid sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is necessary for expression of a coding sequence, and may also include additional components whose presence is advantageous, for example, leader sequences and fusion partner sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

As used herein, the term "expression cassette" refers to a molecule comprising at least one coding sequence operably linked to a control sequence which includes all nucleotide sequences required for the transcription of cloned copies of the coding sequence and the translation of the mRNAs in an appropriate host cell. Such expression cassettes can be used to express eukaryotic genes in a variety of hosts such as bacteria, blue-green algae, plant cells, yeast cells, insect cells and animal cells. Under the invention, expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

By "vector" is meant any genetic element, such as a plasmid, phage, transposon, cosmid, chromosome, virus etc., which is capable of replication when associated with the proper control elements and which can transfer gene sequences between cells. Thus, the term includes cloning and expression vehicles, as well as viral vectors.

"Recombinant host cells", "host cells," "cells," "cell cultures," and other such terms denote, for example, microorganisms, insect cells, and mammalian cells, that can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Examples for mammalian host cells include Chinese hamster ovary (CHO) and monkey kidney (COS) cells.

Specifically, as used herein, "cell line," refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. The term "cell lines" also includes immortalized cells.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

B. General Methods

The present invention is based on the generation of novel cross-genotype reactive human monoclonal antibody molecules specific to the HCV E2 envelope glycoprotein. The monoclonal antibodies are obtained using a combinatorial antibody library constructed from a nonimmunized source, and are useful in the prevention, therapy and diagnosis of HCV infection in mammalian subjects. More particularly, the monoclonal antibodies are obtained from combinatorial libraries expressing Fab molecules on the surface of filamentous DNA bacteriophage using antigen selection techniques.

Preparation of Combinatorial Libraries

Combinatorial libraries for the purposes of the present invention can be constructed using known techniques, such as those described by Chanock et al. (1993) *Infect Agents Dis* 2:118–131 and Barbas, III et al. (1995) *Methods: Comp. Meth Enzymol* 8:94–103. Antibody-producing cells can be obtained from an unimmunized, HCV-infected donor from, e.g., plasma, serum, spinal fluid, lymph fluid, the external sections of the respiratory, intestinal and genitourinary tracts, tears, saliva, milk, white blood cells and myelomas. Preferably, the antibody-producing cell source is lymphocytes that have been obtained from a bone marrow or peripheral blood sample of an unimmunized subject.

Lymphocytes can be obtained from the sample and total RNA isolated and extracted using known methods. See, e.g., Chomczynski et al. (1987) *Anal Biochem* 162:156–159. The RNA can be reverse-transcribed into first strand CDNA using oligo-dT priming. The DNA encoding immunoglobulin heavy (Fd) and light chain fragments can be amplified using the polymerase chain reaction (PCR) to provide all of the genetic material necessary to produce Fab antigen-binding molecules. Saiki, et al. (1986) *Nature* 324:163, Scharf et al. (1986) *Science* 233:1076–1078 and U.S. Pat. Nos. 4,683,195 and 4,683,202. In conducting the PCR amplification, a number of known primers can preferably be used to select for $\gamma 1$ heavy chain and $\kappa$ light chain sequences. Persson et al. (1991) *Proc Natl Acad Sci USA* 88:2432–2436, Kang et al. (1991) *Methods: Comp. Meth Enzymol* 2:111–118. The PCR products are pooled separately into heavy and light chain DNA preparations, and then purified, for example, using gel electrophoresis. The purified heavy and light chain DNA molecules are then digested with suitable restriction enzymes, and the digested products purified and ligated into a suitable phagemid vector system. Yang et al. (1995) *J Mol Biol* 254:392–403, Barbas, III et al. (1995) *Methods: Comp. Meth Enzymol* 8:94–103, Barbas, III et al. (1991) *Proc Natl Acad Sci USA* 88:7978–7982. A number of suitable phagemid vector systems are known in the art; however, a particularly preferred vector for use herein is the pComb3H vector (Available from New England Biolabs) which has been previously described. Barbas, III et al. (1995), supra. When the Pcomb3h phagemid vector is used, heavy chain DNA is cloned into the subject phagemid adjacent to, and upstream of, the sequence for the C-terminal anchorage domain of the phagemid coat protein III (cpIII). The cpiii protein is an integral membrane protein, and thus serves as a membrane anchor for the Fab assembly.

The vectors generally include selectable markers known in the art. For example, the Pcomb3h phagemid vector contains the bacterial ampicillin resistance gene (B-lactamase). The vector will also include appropriate first and second leader sequences, respectively arranged upstream of the insertion sites for the heavy and light chain coding sequences, whereby expression products from the heavy and light chain coding regions are targeted to the periplasm when produced in a suitable host cell. In Pcomb3h, these leader sequences are pelB sequences, omp A sequences or combinations thereof.

The phagemid vector system containing the human immunoglobulin DNA is then introduced into a suitable bacterial host cell (for example using electrophoresis), wherein the phagemid expresses a heavy chain-cpiii fusion polypeptide and a light chain polypeptide, each of which are targeted to the periplasm of the host cell by their associated leader sequences. The transfected bacterial host cell containing the phagemid vector is selected by growth in a suitable medium containing a selective agent corresponding to the selectable marker of the phagemid vector (e.g., ampicillin).

Rescue of the phagemid DNA is conducted using known techniques. In particular, the transfected host cell is infected with a helper phage which encodes a number of expression products necessary in trans for packaging the phagemid DNA into recombinant virus particles. Single-stranded copies of the phagemid DNA are thus packaged into viral particles which, upon leaving the host cell, incorporate phage cpVIII molecules and are capped by a limited number of phage cpiii molecules—some of which cpviii and cpiii molecules are linked to Fab molecules. Recombinant phage particles displaying Fab molecules (termed "phage-Fabs") contain the corresponding heavy and light chain genes within the packaged genome.

When the above technique is practiced using an initial library of phagemids, the rescue process generates a library of recombinant phage which display Fab molecules (a phage display library). The rescue process further results in amplification of the initial library, such that multiple copies of each recombinant phage clone (along with each set of immunoglobulin heavy and light chain binding portions) are generated. The phage display library is then "panned" against HCV E2 antigen to select for Fab molecules which are capable of selectively binding to that antigen. More particularly, the panning procedure can be conducted by applying a suspension containing the phage display library onto HCV E2 antigen that has been immobilized to a plastic reaction vessel according to known methods. Burton et al. (1991) *Proc Natl Acad Sci USA* 88:10134–10137. After incubation under suitable binding conditions, non-specifically bound phage particles are removed by repeated washings. The resulting HCV E2-antigen specific phage-Fabs are then eluted from the insoluble antigen using low Ph, or in the presence of excess soluble E2 antigen. The panning procedure is repeated several times, wherein bacterial host cells are infected by the eluted phage after each round of panning to propagate phage-Fab clones for each subsequent round of panning. Samuelsson et al. (1995) *Virology* 207:495–502.

In the present invention, the panning procedure was specifically developed to select for highly potent, cross-genotype reactive Fab molecules specific for HCV E2 antigen. In particular, the genotype of serum HCV of the unimmunized, HCV-infected human subject from which the antibody-producing cells were obtained was determined using known methods. Widell et al. (1994) *J Med Virol* 44:272–279. Selection for strain cross-reactivity was provided by experimental design, wherein the panning procedure was conducted using HCV E2 antigen derived from a different HCV genotype than that of the HCV from the infected human donor. Furthermore, the E2 antigen used in the panning procedures was selected so as to provide HCV E2 antigen in substantially the same conformation as expected for that antigen in vivo.

Two different recombinant HCV envelope protein preparations were used to provide the selecting antigen in the above-described panning procedure, a "conformational" CHO E2 molecule, and a CHO E1/E2 complex. The conformational E2 molecule was constructed, expressed and secreted from recombinant CHO cells as previously described in Spaete et al. (1992) *Virology* 188:819–830, then purified using known methods (Rosa et al. (1996) *Proc Natl Acad Sci USA* 93:1759–1763). A recombinant complexed E1/E2 preparation was constructed and expressed from recombinant CHO cells as described in Spaete et al. (1992) supra, then purified using known methods (Choo et al. (1994) *Proc Natl Acad Sci USA* 91:1294–1298). Once purified, the selecting antigens were immobilized to a plastic reaction vessel as described above.

Individual clones exhibiting superior binding affinity for the selecting antigen were selected, and expressed by growing infected host cells in the selective medium until a suitable volume of cells was reached. The bacterial host cells were pelleted and then resuspended in medium. After suitable incubation, the cells were spun down, and the periplasmic content released by freeze-thawing techniques. After the bacterial debris was removed by centrifugation, the Fab-containing supernatant was transferred to suitable containers, and stored for future use.

Once the selected Fabs are expressed, binding characteristics of the selected Fab molecules can be determined. In particular, the affinity of the Fab molecules for HCV E2 antigen was determined herein using an inhibition ELISA technique. See, e.g., Persson et al. (1991) *Proc Natl Acad Sci USA* 88:2432–2436, Rath et al. (1988) *J Immun Methods* 106:245–249. Clones that expressed Fab molecules of high potency (e.g., an affinity of at least about $1\times10^7$ $M^{-1}$, and preferably at least about $1.7\times10^7$ $M^{-1}$ as determined by inhibition ELISA) were identified for sequencing.

Phage (plasmid) DNA from clones which exhibited high potency binding in the panning selection process was isolated, and single stranded DNA was obtained by PCR using primers (one of which, e.g., is biotinylated at the 5' end) that hybridize upstream and downstream of the immunoglobulin cloning regions. After PCR, single stranded DNA was obtained by denaturing the DNA under alkaline conditions, and absorbing biotinylated DNA strands onto a solid support. Dideoxy sequencing reactions were performed according to known methods (Sanger et al. (1977)

*Proc Natl Acad Sci USA* 74:5463–5467) using labeled primers hybridizing 3' of the junction between the variable and constant regions. Kabat et al., in *Sequences of Proteins of Immunological Interest*, 4th ed., (U.S. Dept. of Health and Human Services, U.S. Government Printing Office, 1987). The reaction products were run on an automated sequencer (for example, A.L.F. available from Pharmacia Biotech). The nucleic acid sequence information thus obtained was analyzed to provide coding sequences for the heavy chain and light chain portions of the selected monoclonal Fab molecules. Multiple copies of the same clones were identified by comparisons of sequence data. Further, the deduced amino acid sequences were obtained using known methods.

Using the above nucleic acid sequence information, coding sequences for the Fab molecules can also be produced synthetically using known methods. Nucleotide sequences can be designed with the appropriate codons for the particular amino acid sequence desired. In general, one will select preferred codons for the intended host in which the sequences will be expressed. The complete sequences are generally assembled from overlapping oligonucleotides prepared by standard methods and assembled into complete coding sequences. See, e.g., Edge (1981) *Nature* 292:756; Nambair et al. (1984) *Science* 223:1299; Jay et al. (1984) *J. Biol. Chem.* 259:6311.

Expression Systems

Once the coding sequences for the heavy and light chain portions of the Fab molecules are isolated or synthesized, they can be cloned into any suitable vector or replicon for expression, for example, bacterial, mammalian, yeast and viral expression systems can be used. Numerous cloning vectors are known to those of skill in the art and are described below. The selection of an appropriate cloning vector is a matter of choice.

i. Expression in Bacterial Cells

Bacterial expression systems can be used to produce the Fab molecules. Control elements for use in bacterial systems include promoters, optionally containing operator sequences, and ribosome binding sites. Useful promoters include sequences derived from sugar metabolizing enzymes, such as galactose, lactose (lac) and maltose. Additional examples include promoter sequences derived from biosynthetic enzymes such as tryptophan (trp), the β-lactamase (bla) promoter system, bacteriophage λPL, and T7. In addition, synthetic promoters can be used, such as the tac promoter. The β-lactamase and lactose promoter systems are described in Chang et al., *Nature* (1978) 275:615, and Goeddel et al., *Nature* (1979) 281: 544; the alkaline phosphatase, tryptophan (trp) promoter system are described in Goeddel et al., *Nucleic Acids Res.* (1980) 8:4057 and EP 36,776 and hybrid promoters such as the tac promoter is described in U.S. Pat. No. 4,551,433 and deBoer et al., *Proc. Natl. Acad. Sci. USA* (1983) 80:21–25. However, other known bacterial promoters useful for expression of eukaryotic proteins are also suitable. A person skilled in the art would be able to operably ligate such promoters to the Fab molecules for example, as described in Siebenlist et al., *Cell* (1980) 20:269, using linkers or adapters to supply any required restriction sites. Promoters for use in bacterial systems also generally contain a Shine-Dalgarno (SD) sequence operably linked to the DNA encoding the Fab molecule. For prokaryotic host cells that do not recognize and process the native polypeptide signal sequence, the signal sequence can be substituted by a prokaryotic signal sequence selected, for example, from the group of the alkaline phosphatase, penicillinase, lpp, or heat stable enterotoxin II leaders. The origin of replication from the plasmid pBR322 is suitable for most Gram-negative bacteria.

The foregoing systems are particularly compatible with *Escherichia coli*. However, numerous other systems for use in bacterial hosts including Gram-negative or Gram-positive organisms such as Bacillus spp., Streptococcus spp., Streptomyces spp., Pseudomonas species such as *P. aeruginosa*, *Salmonella typhimurium*, or *Serratia marcescans*, among others. Methods for introducing exogenous DNA into these hosts typically include the use of $CaCl_2$ or other agents, such as divalent cations and DMSO. DNA can also be introduced into bacterial cells by electroporation, nuclear injection, or protoplast fusion as described generally in Sambrook et al. (1989), cited above. These examples are illustrative rather than limiting. Preferably, the host cell should secrete minimal amounts of proteolytic enzymes. Alternatively, in vitro methods of cloning, e.g., PCR or other nucleic acid polymerase reactions, are suitable.

Prokaryotic cells used to produce the Fab molecules of this invention are cultured in suitable media, as described generally in Sambrook et al., cited above.

ii. Expression in Yeast Cells

Yeast expression systems can also be used to produce the subject Fab molecules. Expression and transformation vectors, either extrachromosomal replicons or integrating vectors, have been developed for transformation into many yeasts. For example, expression vectors have been developed for, among others, the following yeasts: *Saccharomyces cerevisiae*, as described in Hinnen et al., *Proc. Natl. Acad. Sci. USA* (1978) 75:1929; Ito et al., *J. Bacteriol.* (1983) 153:163; *Candida albicans* as described in Kurtz et al., *Mol. Cell. Biol.* (1986) 6:142; *Candida maltosa*, as described in Kunze et al., *J. Basic Microbiol.* (1985) 25:141; *Hansenula polymorpha*, as described in Gleeson et al., *J. Gen. Microbiol.* (1986) 132:3459 and Roggenkamp et al., *Mol. Gen. Genet.* (1986) 202:302; *Kluyveromyces fragilis*, as described in Das et al., *J. Bacteriol.* (1984) 158:1165; *Kluyveromyces lactis*, as described in De Louvencourt et al., *J. Bacteriol.* (1983) 154:737 and Van den Berg et al., *Bio/Technology* (1990) 8:135; *Pichia guillerimondii*, as described in Kunze et al., *J. Basic Microbiol.* (1985) 25:141; *Pichia pastoris*, as described in Cregg et al., *Mol. Cell. Biol.* (1985) 5:3376 and U.S. Pat. Nos. 4,837,148 and 4,929,555; *Schizosaccharomyces pombe*, as described in Beach and Nurse, *Nature* (1981) 300:706; and *Yarrowia lipolytica*, as described in Davidow et al., *Curr. Genet.* (1985) 10:380 and Gaillardin et al., *Curr. Genet.* (1985) 10:49, Aspergillus hosts such as *A. nidulans*, as described in Ballance et al., *Biochem. Biophys. Res. Commun.* (1983) 112:284–289; Tilburn et al., *Gene* (1983) 26:205–221 and Yelton et al., *Proc. Natl. Acad. Sci. USA* (1984) 81:1470–1474, and *A. niger*, as described in Kelly and Hynes, *EMBO J.* (1985) 4:475479; *Trichoderma reesia*, as described in EP 244,234, and filamentous fungi such as, e.g, Neurospora, Penicillium, Tolypocladium, as described in WO 91/00357.

Control sequences for yeast vectors are known and include promoter regions from genes such as alcohol dehydrogenase (ADH), as described in EP 284,044, enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK), as described in EP 329,203. The yeast PHO5 gene, encoding acid phosphatase, also provides useful promoter sequences, as described in Myanohara et al., *Proc. Natl. Acad. Sci. USA* (1983) 80:1. Other suitable promoter sequences for use with yeast hosts include the promoters for 3-phosphoglycerate kinase, as described in Hitzeman et al., *J. Biol. Chem.* (1980) 255:2073, or other glycolytic enzymes, such as pyruvate decarboxylase, triosephosphate isomerase, and phosphoglucose isomerase, as described in Hess et al., *J. Adv. Enzyme Reg.* (1968) 7:149 and Holland et al., *Biochemistry* (1978) 17:4900. Inducible yeast promoters having the additional advantage of transcription controlled by growth conditions, include from the list above and others the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman, EP 073,657. Yeast enhancers also are advantageously used with yeast promoters. In addition, synthetic promoters which do not occur in nature also function as yeast promoters. For example, upstream activating sequences (UAS) of one yeast promoter may be joined with the transcription activation region of another yeast promoter, creating a synthetic hybrid promoter. Examples of such hybrid promoters include the ADH regulatory sequence linked to the GAP transcription activation region, as described in U.S. Pat. Nos. 4,876,197 and 4,880,734. Other examples of hybrid promoters include promoters which consist of the regulatory sequences of either the ADH2, GAL4, GAL10, or PHO5 genes, combined with the transcriptional activation region of a glycolytic enzyme gene such as GAP or PyK, as described in EP 164,556. Furthermore, a yeast promoter can include naturally occurring promoters of non-yeast origin that have the ability to bind yeast RNA polymerase and initiate transcription.

Other control elements which may be included in the yeast expression vectors are terminators, for example, from GAPDH and from the enolase gene, as described in Holland et al., *J. Biol. Chem.* (1981) 256:1385, and leader sequences which encode signal sequences for secretion. DNA encoding suitable signal sequences can be derived from genes for secreted yeast proteins, such as the yeast invertase gene as described in EP 012,873 and JP 62,096,086 and the α-factor gene, as described in U.S. Pat. Nos. 4,588,684, 4,546,083 and 4,870,008; EP 324,274; and WO 89/02463. Alternatively, leaders of non-yeast origin, such as an interferon leader, also provide for secretion in yeast, as described in EP 060,057.

Methods of introducing exogenous DNA into yeast hosts are well known in the art, and typically include either the transformation of spheroplasts or of intact yeast cells treated with alkali cations. Transformations into yeast can be carried out according to the method described in Van Solingen et al., *J. Bact.* (1977) 130:946 and Hsiao et al., *Proc. Natl. Acad. Sci. USA* (1979) 76:3829. However, other methods for introducing DNA into cells such as by nuclear injection, electroporation, or protoplast fusion may also be used as described generally in Sambrook et al., cited above.

For yeast secretion the native polypeptide signal sequence may be substituted by the yeast invertase, α-factor, or acid phosphatase leaders. The origin of replication from the 2µ plasmid origin is suitable for yeast. A suitable selection gene for use in yeast is the trpl gene present in the yeast plasmid described in Kingsman et al., *Gene* (1979) 7:141 or Tschemper et al., *Gene* (1980) 10:157. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 Gene.

For intracellular production of the present polypeptides in yeast, a sequence encoding a yeast protein can be linked to a coding sequence for the Fab molecule to produce a fusion protein that can be cleaved intracellularly by the yeast cells upon expression. An example, of such a yeast leader sequence is the yeast ubiquitin gene.

iii. Expression in Insect Cells

The Fab molecules can also be produced in insect expression systems. For example, baculovirus expression vectors (BEVs) are recombinant insect viruses in which the coding sequence for a foreign gene to be expressed is inserted behind a baculovirus promoter in place of a viral gene, e.g., polyhedrin, as described in Smith and Summers, U.S. Pat. No., 4,745,051.

An expression construct herein includes a DNA vector useful as an intermediate for the infection or transformation of an insect cell system, the vector generally containing DNA coding for a baculovirus transoriptional promoter, optionally but preferably, followed downstream by an insect signal DNA sequence capable of directing secretion of a desired protein, and a site for insertion of the foreign gene encoding the foreign protein, the signal DNA sequence and the foreign gene being placed under the transcriptional control of a baculovirus promoter, the foreign gene herein being the coding sequence of the Fab molecule.

The promoter for use herein can be a baculovirus transcriptional promoter region derived from any of the over 500 baculoviruses generally infecting insects, such as, for example, the Orders Lepidoptera, Diptera, Orthoptera, Coleoptera and Hymenoptera including, for example, but not limited to the viral DNAs of *Autographo californica* MNPV, *Bombyx mori* NPV, *rrichoplusia ni* MNPV, *Rachlplusia ou* MNPV or *Galleria mellonella* MNPV, *Aedes aegypti*, *Drosophila melanogaster*, *Spodoptera frugiperda*, and *Trichoplusia ni*. Thus, the baculovirus transcriptional promoter can be, for example, a baculovirus immediate-early gene IEI or IEN promoter; an immediate-early gene in combination with a baculovirus delayed-early gene promoter region selected from the group consisting of a 39K and a HindIII fragment containing a delayed-early gene; or a baculovirus late gene promoter. The immediate-early or delayed-early promoters can be enhanced with transcriptional enhancer elements.

Particularly suitable for use herein is the strong polyhedrin promoter of the baculovirus, which directs a high level of expression of a DNA insert, as described in Friesen et al. (1986) "The Regulation of Baculovirus Gene Expression" in: THE MOLECULAR BIOLOGY OF BACULOVIRUSES (W. Doerfler, ed.); EP 127,839 and EP 155,476; and the promoter from the gene encoding the p10 protein, as described in Vlak et al., *J. Gen. Virol.* (1988) 69:765–776.

The plasmid for use herein usually also contains the polyhedrin polyadenylation signal, as described in Miller et al., *Ann. Rev. Microbiol.* (1988) 42:177 and a procaryotic ampicillin-resistance (amp) gene and an origin of replication for selection and propagation in *E. coli*. DNA encoding suitable signal sequences can also be included and is generally derived from genes for secreted insect or baculovirus proteins, such as the baculovirus polyhedrin gene, as described in Carbonell et al., *Gene* (1988) 73:409, as well as mammalian signal sequences such as those derived from genes encoding human α-interferon as described in Maeda et al., *Nature* (1985) 315:592–594; human gastrin-releasing peptide, as described in Lebacq-Verheyden et al., *Mol. Cell. Biol.* (1988) 8:3129; human IL-2, as described in Smith et al., *Proc. Natl. Acad. Sci. USA* (1985) 82:8404; mouse IL-3, as described in Miyajima et al., *Gene* (1987) 58:273; and human glucocerebrosidase, as described in Martin et al., *DNA* (1988) 7:99.

Numerous baculoviral strains and variants and corresponding permissive insect host cells from hosts such as

*Spodoptera frugiperda* (caterpillar), *Aedes aegypti* (mosquito), *Aedes albopictus* (mosquito), *Drosophila melanogaster* (fruitfly), and *Bombyx mori* host cells have been identified and can be used herein. See, for example, the description in Luckow et al., *Bio/Technology* (1988) 6:47–55, Miller et al., in GENETIC ENGINEERING (Setlow, J. K. et al. eds.), Vol. 8 (Plenum Publishing, 1986), pp. 277–279, and Maeda et al., *Nature* (1985) 315:592–594. A variety of such viral strains are publicly available, e.g., the L-1 variant of *Autographa californica* NPV and the Bm-5 strain of *Bombyx mori* NPV. Such viruses may be used as the virus for transfection of host cells such as *Spodoptera frugiperda* cells.

Other baculovirus genes in addition to the polyhedrin promoter may be employed in a baculovirus expression system. These include immediate-early (alpha), delayed-early (beta), late (gamma), or very late (delta), according to the phase of the viral infection during which they are expressed. The expression of these genes occurs sequentially, probably as the result of a "cascade" mechanism of transcriptional regulation. Thus, the immediate-early genes are expressed immediately after infection, in the absence of other viral functions, and one or more of the resulting gene products induces transcription of the delayed-early genes. Some delayed-early gene products, in turn, induce transcription of late genes, and finally, the very late genes are expressed under the control of previously expressed gene products from one or more of the earlier classes. One relatively well defined component of this regulatory cascade is IEI, a preferred immediate-early gene of *Autographo californica* nuclear polyhedrosis virus (AcMNPV). IEI is pressed in the absence of other viral functions and encodes a product that stimulates the transcription of several genes of the delayed-early class, including the preferred 39K gene, as described in Guarino and Summers, *J. Virol.* (1986) 57:563–571 and *J. Virol.* (1987) 61:2091–2099 as well as late genes, as described in Guanno and Summers, *Virol.* (1988) 162:444–451.

Immediate-early genes as described above can be used in combination with a baculovirus gene promoter region of the delayed-early category. Unlike the immediate-early genes, such delayed-early genes require the presence of other viral genes or gene products such as those of the immediate-early genes. The combination of immediate-early genes can be made with any of several delayed-early gene promoter regions such as 39K or one of the delayed-early gene promoters found on the HindIII fragment of the baculovirus genome. In the present instance, the 39 K promoter region can be linked to the foreign gene to be expressed such that expression can be further controlled by the presence of IEI, as described in L. A. Guarino and Summers (1986a), cited above; Guarino & Summers (1986b) *J. Virol.* (1986) 60:215–223, and Guarino et al. (1986c) *J. Virol.* (1986) 60:224–229.

Additionally, when a combination of immediate-early genes with a delayed-early gene promoter region is used, enhancement of the expression of heterologous genes can be realized by the presence of an enhancer sequence in direct cis linkage with the delayed-early gene promoter region. Such enhancer sequences are characterized by their enhancement of delayed-early gene expression in situations where the immediate-early gene or its product is limited. For example, the hr5 enhancer sequence can be linked directly, in cis, to the delayed-early gene promoter region, 39K, thereby enhancing the expression of the cloned heterologous DNA as described in Guarino and Summers (1986a), (1986b), and Guarino et al. (1986).

The polyhedrin gene is classified as a very late gene. Therefore, transcription from the polyhedrin promoter requires the previous expression of an unknown, but probably large number of other viral and cellular gene products. Because of this delayed expression of the polyhedrin promoter, state-of-the-art BEVS, such as the exemplary BEV system described by Smith and Summers in, for example, U.S. Pat. No. , 4,745,051 will express foreign genes only as a result of gene expression from the rest of the viral genome, and only after the viral infection is well underway. This represents a limitation to the use of existing BEVs. The ability of the host cell to process newly synthesized proteins decreases as the baculovirus infection progresses. Thus, gene expression from the polyhedrin promoter occurs at a time when the host cell's ability to process newly synthesized proteins is potentially diminished for certain proteins such as human tissue plasminogen activator. As a consequence, the expression of secretory glycoproteins in BEV systems is complicated due to incomplete secretion of the cloned gene product, thereby trapping the cloned gene product within the cell in an incompletely processed form.

While it has been recognized that an insect signal sequence can be used to express a foreign protein that can be cleaved to produce a mature protein, the present invention can also be practiced with a mammalian signal sequence.

An exemplary insect signal sequence suitable herein is the sequence encoding for a Lepidopteran adipokinetic hormone (AKH) peptide. The AKH family consists of short blocked neuropeptides that regulate energy substrate mobilization and metabolism in insects. In a preferred embodiment, a DNA sequence coding for a Lepidopteran *Manduca sexta* AKH signal peptide can be used. Other insect AKH signal peptides, such as those from the Orthoptera *Schistocerca gregaria* locus can also be employed to advantage. Another exemplary insect signal sequence is the sequence coding for Drosophila cuticle proteins such as CPI, CP2, CP3 or CP4.

Currently, the most commonly used transfer vector that can be used herein for introducing foreign genes into AcNPV is pAc373. Many other vectors, known to those of skill in the art, can also be used herein. Materials and methods for baculovirus/insect cell expression systems are commercially available in a kit form from companies such as Invitrogen (San Diego Calif.) ("MaxBac" kit). The techniques utilized herein are generally known to those skilled in the art and are fully described in Summers and Smith, A MANUAL OF METHODS FOR BACULOVIRUS VECTORS AND INSECT CELL CULTURE PROCEDURES, Texas Agricultural Experiment Station Bulletin No. 1555, Texas A&M University (1987); Smith et al., *Mol. Cell. Biol.* (1983), and Luckow and Summers (1989). These include, for example, the use of pVL985 which alters the polyhedrin start codon from ATG to ATT, and which introduces a BamHI cloning site 32 basepairs downstream from the ATT, as described in Luckow and Summers, *Virology* (1989) 17:31.

Thus, for example, for insect cell expression of the present polypeptides, the desired DNA sequence can be inserted into the transfer vector, using known techniques. An insect cell host can be cotransformed with the transfer vector containing the inserted desired DNA together with the genomic DNA of wild type baculovirus, usually by cotransfection. The vector and viral genome are allowed to recombine resulting in a recombinant virus that can be easily identified and purified. The packaged recombinant virus can be used to infect insect host cells to express a Fab molecule.

Other methods that are applicable herein are the standard methods of insect cell culture, cotransfection and preparation of plasmids are set forth in Summers and Smith (1987), cited above. This reference also pertains to the standard methods of cloning genes into AcMNPV transfer vectors, plasmid DNA isolation, transferring genes into the AcmMNPV genome, viral DNA purification, radiolabeling recombinant proteins and preparation of insect cell culture media. The procedure for the cultivation of viruses and cells are described in Volkman and Summers, *J. Virol.* (1975) 19:820–832 and Volkman et al., *J. Virol.* (1976) 19:820–832.

iv. Expression in Mammalian Cells

Mammalian expression systems can also be used to produce the Fab molecules. Typical promoters for mammalian cell expression include the SV40 early promoter, the CMV promoter, the mouse mammary tumor virus LTR promoter, the adenovirus major late promoter (Ad MLP), and the herpes simplex virus promoter, among others. Other non-viral promoters, such as a promoter derived from the murine metallothionein gene, will also find use in mammalian constructs. Mammalian expression may be either constitutive or regulated (inducible), depending on the promoter. Typically, transcription termination and polyadenylation sequences will also be present, located 3' to the translation stop codon. Preferably, a sequence for optimization of initiation of translation, located 5' to the Fab coding sequence, is also present. Examples of transcription terminator/polyadenylation signals include those derived from SV40, as described in Sambrook et al. (1989) MOLECULAR CLONING: A LABORATORY MANUAL, 2d edition, (Cold Spring Harbor Press, Cold Spring Harbor, N.Y.). Introns, containing splice donor and acceptor sites, may also be designed into the constructs of the present invention.

Enhancer elements can also be used herein to increase expression levels of the mammalian constructs. Examples include the SV40 early gene enhancer, as described in Dijkema et al., *EMBO J.* (1985) 4: 761 and the enhancer/promoter derived from the long terminal repeat (LTR) of the Rous Sarcoma Virus, as described in Gorman et al., *Proc. Natl. Acad. Sci. USA* (1982b) 79:6777 and human cytomegalovirus, as described in Boshart et al., *Cell* (1985) 41:521. A leader sequence can also be present which includes a sequence encoding a signal peptide, to provide for the secretion of the foreign protein in mammalian cells. Preferably, there are processing sites encoded between the leader fragment and the gene of interest such that the leader sequence can be cleaved either in vivo or in vitro. The adenovirus tripartite leader is an example of a leader sequence that provides for secretion of a foreign protein in mammalian cells.

There exist expression vectors that provide for the transient expression in mammalian cells of DNA encoding the Fab molecules. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Once complete, the mammalian expression vectors can be used to transform any of several mammalian cells. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei. General aspects of mammalian cell host system transformations have been described by Axel in U.S. Pat. No. 4,399,216. A synthetic lipid particularly useful for polynucleotide transfection is N-[1-(2,3-dioleyloxy)propyl]-N,N,N-trimethylammonium chloride, which is commercially available under the name Lipofectin® (available from BRL, Gaithersburg, Md.), and is described by Felgner et al., *Proc. Natl. Acad. Sci. USA* (1987) 84:7413.

Mammalian cell lines available as hosts for expression are also known and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), human embryonic kidney cells, baby hamster kidney cells, mouse sertoli cells, canine kidney cells, buffalo rat liver cells, human lung cells, human liver cells, mouse mammary tumor cells, as well as others. The mammalian host cells used to produce the Fab molecules of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEMl, Sigma) are suitable for culturing the host cells. In addition, any of the media described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, or 4,560,655, WO 90/103430, WO 87/00195, and U.S. Pat. No. RE 30,985, may be used as culture media for the host cells. Any of these media may be supplemented as necessary with hormones and/or other growth factors such as insulin, transferring, or epidermal growth factor, salts (such as sodium chloride, calcium, magnesium, and phosphate), buffers (such as HEPES), nucleosides (such as adenosine and thymidine), antibiotics (such as Gentamycin(tm) M drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, Ph, and the like, are those previously used with the host cell selected for expression, and will be apparent to the ordinarily skilled artisan.

Preparing Specific Binding Molecules

Using the above techniques, a number of specific binding molecules that exhibit immunological binding affinity for HCV E2 antigen can be provided. In particular, depending on the expression system and host selected, soluble Fab specific binding molecules can be readily produced by growing host cells transformed by an expression vector described above under conditions whereby the heavy and light chain portions are expressed. Heterodimers comprising noncovalently associated heavy and light chains can be isolated from the host cells and purified. Since the present invention also provides for the optional secretion of the heavy and light chain polypeptides, the Fab heterodimers can be purified directly from the media. The selection of the appropriate growth conditions and recovery methods are within the skill of the art.

In addition, the Fab molecules of the present invention can be produced using conventional methods of protein synthesis, based on the ascertained amino acid sequences. In general, these methods employ the sequential addition of one or more amino acids to a growing peptide chain.

Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis,* 2nd Ed., Pierce Chemical Co., Rockford, Ill. (1984) and G. Barany and R. B. Merrifield, *The Peptides: Analysis, Synthesis, Biology,* editors E. Gross and J. Meienhofer, Vol. 2, Academic Press, New York, (1980), pp. 3–254, for solid phase peptide synthesis techniques; and M. Bodansky, *Principles of Peptide Synthesis,* Springer-Verlag, Berlin (1984) and E. Gross and J. Meienhofer, Eds., *The Peptides: Analysis, Synthesis, Biology,* supra, Vol. 1, for classical solution synthesis.

Recombinant human monoclonal antibody specific binding molecules can be prepared from the Fab molecules using known techniques. Bender et al. (1992) *Hum Antibod Hybridomas* 4:74. In particular, the coding sequence for the heavy chain portion of a selected Fab clone can be inserted into an expression vector along with the coding sequence for the constant domains of a human Ig heavy chain, using the various recombinant techniques described above. For example, the mammalian expression vector pSG5 (Green et al. (1988) *Nucleic Acids Res* 16:369) can be used for this purpose. Cloning involves overlap PCR to remove the bacterial leader sequence (from the phagemid vector) and to modify the N-terminus of the heavy chain coding sequence to a human consensus sequence. The coding sequence for the light chain portion of the selected Fab clone can likewise be N-terminal modified to include a human consensus sequence, and cloned into an expression vector such as PSG5. The PSG5 vectors contain an SV40 origin of replication such that, on cotransfection of the heavy and light chain vectors into mammalian cells, such as COS-7 cells, functional antibody molecule production can be confirmed. Burton et al. (1994) *Science* 266:1024–1027. The heavy and light chains can subsequently be cloned into separate cloning vectors, and either the heavy or the light chain coding sequence subcloned into the other vector to provide a combinatorial plasmid. For example, the heavy and light chain coding sequences can be respectively inserted into pEE6 and pEE12 vectors (Bebbington et al. (1992) *Bio/Technology* 10:169) which include a human cytomegalovirus promoter and the glutamine synthetase selectable marker. The heavy chain, along with control elements from the PEE6 vector can then be subcloned into the PEE12 vector to provide a combinatorial plasmid. The combinatorial plasmid can be expressed in a CHO cell expression system. Those clones from the CHO expression system which provide sufficient levels of recombinant antibody production can be selected for scale-up. The recombinant antibodies expressed in the CHO-system can be purified using known techniques (e.g., affinity chromatography using protein A), and the binding affinity of the recombinant specific binding molecules assessed using an ELISA inhibition assay as described above.

Recombinant F(ab')$_2$ and recombinant Fv specific binding molecules can also be prepared from the phage-derived Fab clones using known techniques. Fv molecules generally comprise a non-covalently bound heavy chain:light chain heterodimer which includes the antigen-binding portion of the Fab molecule and retains much of the antigen recognition and binding capabilities of native antibody molecules. Inbar et al. (1972) *Proc. Nat. Acad. Sci. USA* 69:2659–2662; Hochman et al. (1976) *Biochem* 15:2706–2710; and Ehrlich et al. (1980) *Biochem* 19:4091–4096. Typically, the above-noted recombinant techniques used to construct the recombinant monoclonal antibodies can be modified to provide the truncated specific binding molecules. These molecules can also be cloned into CHO expression systems, purified and characterized as above.

The phage-derived Fab clones can further be used to provide single chain Fv (Sfv) molecules using known techniques. These Sfv molecules comprise a covalently linked heavy chain:light chain heterodimer which is expressed from a gene fusion including the heavy and light chain coding sequences obtained from the phage-derived Fab molecule, wherein the chains are linked by a peptide-encoding linker. Huston et al. (1988) *Proc. Nat. Acad. Sci. USA* 85(16):5879–5883. A number of methods have been described to discern chemical structures for converting the naturally aggregated—but chemically separated—heavy and light chains into an Sfv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In the practice of the invention, recombinant DNA design methods are used to develop appropriate chemical structures for linking the heavy and light chains into the Sfv binding molecule. Design criteria include determination of the appropriate length to span the distance between the C-terminus of one chain and the N-terminus of the other, wherein the linker is generally formed from small hydrophilic amino acid residues that do not tend to coil or form secondary structures. Such methods have been described in the art. See, e.g., U.S. Pat. Nos. 5,091,513 and 5,132,405 to Huston et al.; and U.S. Pat. No. 4,946,778 to Ladner et al.

The first general step of linker design involves identification of plausible sites to be linked. Appropriate linkage sites on each of the immunoglobulin chains include those which will result in the minimum loss of residues from the heavy and light chains, and which will necessitate a linker having a minimum number of residues consistent with the need for molecule stability. A pair of sites defines a "gap" to be linked. Linkers connecting the C-terminus of one chain to the N-terminus of the next generally include hydrophilic amino acids which assume an unstructured configuration in physiological solutions and preferably are free of residues having large side groups which might interfere with proper folding of the heavy and light chains. Thus, suitable linkers would include polypeptide chains of alternating sets of glycine and serine residues, and may include glutamic acid and lysine residues inserted to enhance solubility. One particular linker used in the practice of the invention has the amino acid sequence $[(Gly)_4 Ser]_3$. Another particularly preferred linker has the amino acid sequence comprising 2 or 3 repeats of $[(Ser)_4 Gly]$, such as $[(Ser)_4 Gly]_3$. Nucleotide sequences encoding such linker moieties can be readily provided using various oligonucleotide synthesis techniques known in the art. See, e.g., Sambrook, and Maniatis, supra.

Once the appropriate linker sequence has been ascertained, nucleotide sequences encoding the Sfv molecules can be joined using an overlap PCR approach. See, e.g., Horton et al. (1990) *BioTechniques* 8:528–535. The ends of the light and heavy chains that are to be joined through the selected linker sequence are first extended by PCR amplification of each chain, using primers that contain the terminal sequence of the chain region followed by all or most of the desired linker sequence. After this extension step, the light and heavy chains contain overlapping extensions which jointly contain the entire linker sequence, and which can be annealed at the overlap and extended by PCR to obtain the complete Sfv sequence using methods known in the art. Genes present in expression cassettes comprising the sFv sequence can then be expressed in a suitable expression system, and the sFv molecules produced therefrom can be purified and characterized as described above.

Vaccine Compositions

Therapeutic and prophylactic vaccine compositions are provided herein, which generally comprise mixtures of one or more of the above-described anti-HCV monoclonal antibodies, including Fab molecules, Fv fragments, sFv molecules and combinations thereof. The prophylactic vaccines can be used to prevent HCV infection, and the therapeutic vaccines used to treat individuals following HCV infection. Prophylactic uses include the provision of increased antibody titer to HCV in a vaccinated subject. In this manner, subjects at high risk of contracting HCV infection (e.g., immunocompromised individuals, organ transplant patients, individuals obtaining blood or blood product transfusions, and individuals in close personal contact with HCV-infected individuals) can be provided with passive immunity to the HCV agent. Furthermore, due to the cross-reactivity of the monoclonal antibodies, Fab molecules and sFv molecules produced herein, a level of protection is afforded against a number of heterologous HCV isolates. Other prophylactic uses for the present anti-HCV vaccines includes prevention of HCV disease in an individual after exposure to the infectious agent. Therapeutic uses of the present vaccines involve both reduction and/or elimination of the infectious agent from infected individuals, as well as the reduction and/or elimination of circulating HCV and the possible spread of the disease.

The compositions can be administered in conjunction with ancillary immunoregulatory agents, for example, cytokines, lymphokines, and chemokines, including but not limited to IL-2, modified IL-2 (cys125→ser125), GM-CSF, IL-12, γ-interferon, IP-10, MIP1β and RANTES. When the vaccine compositions are used as therapeutic vaccines, the compositions can be administered in conjunction with known anti-HCV therapeutics, such as α-interferon (α-IFN) therapy which generally entails administration of 3 million units of α-IFN three times a week subcutaneously (Causse et al. (1991) *Gastroenterology* 101:497–502, Davis et al. (1989) *N Engl J Med* 321:1501–1506, Marcellin et al. (1991) *Hepatology* 13:393–397), interferon β (β-IFN) therapy (Omata et al. (1991) *Lancet* 338:914–915), ribivirin therapy (Di Bisceglie et al. (1992) *Hepatology* 16:649–654, Reichard et al. (1991) *Lancet* 337:1058–1061) and antisense therapy (Wakita et al. (1994) *J Biol Chem* 269:14205–14210). Therapeutic vaccine compositions comprising the present monoclonal antibodies can also be used in conjunction with known anti-HCV combination therapies, for example, the combination of α-IFN and ursodiol (Bottelli et al. (1993) (Abstr.) *Gastroenterology* 104:879, O'Brien et al. (1993) (Abstr.) *Gastroenterology* 104:966) and the combination of β-IFN and ribivirin (Kakumu et al. (1993) *Gastroenterology* 105:507–512).

The preparation of vaccine compositions containing one or more antibodies, antibody fragments, sFv molecules or combinations thereof, as the active ingredient is generally known to those of skill in the art. Typically, such vaccines are prepared as injectables (e.g., either as liquid solutions or suspensions or as solid forms suitable for solution or suspension in liquids prior to injection). The compositions will generally also include one or more "pharmaceutically acceptable excipients or vehicles" such as water, saline, dextrose, glycerol, ethanol, or the like and combinations thereof. Additionally, minor amounts of auxiliary substances, such as wetting or emulsifying agents, pH buffering substances, and the like, may be present in such vehicles. The vaccine compositions may be emulsified or the active ingredient (monoclonal antibodies) may be encapsulated in liposomes.

Once formulated, the vaccine compositions are conventionally administered parenterally, e.g., by injection (either subcutaneously or intramuscularly). Additional formulations suitable for other modes of administration include oral and pulmonary formulations, suppositories, and transdermal applications. For suppositories, traditional binders and carriers may include, for example, polyalkylene glycols or triglycerides. Such suppository formulations may be provided from mixtures containing the active ingredient(s) in the range of 0.5% to 10%, preferably 1%–2%. Oral formulations include such normally employed excipients as, for example, pharmaceutical grades of mannitol, lactose, starch, magnesium stearate, sodium saccharine, cellulose, magnesium carbonate, and the like.

The vaccine compositions are administered to the subject to be treated in a manner compatible with the dosage formulation, and in an amount that will be prophylactically and/or therapeutically effective. The amount of the composition to be delivered, generally in the range of from 1 to 500 micrograms of active agent per dose, depends on the subject to be treated, the capacity of the subject's immune system to mount its own immune-responses, and the degree of protection desired. The exact amount necessary will vary depending on the age and general condition of the individual to be treated, the severity of the condition being treated and the particular anti-HCV agent selected and its mode of administration, among other factors. An appropriate effective amount can be readily determined by one of skill in the art. Thus, a "therapeutically effective amount" of the composition will be sufficient to bring about treatment or prevention of HCV disease symptoms, and will fall in a relatively broad range that can be determined through routine trials.

In addition, the vaccine compositions can be given in a single dose schedule, or preferably in a multiple dose schedule. A multiple dose schedule is one in which a primary course of vaccination may be with 1–10 separate doses, followed by other doses given at subsequent time intervals needed to maintain or reinforce the action of the compositions. Thus, the dosage regimen will also, at least in part, be determined based on the particular needs of the subject to be treated and will be dependent upon the judgement of the reasonably skilled practitioner.

Gene Therapy

The recombinant monoclonal antibodies can also be used for gene therapy. In this regard, genes encoding the recombinant antibodies can be introduced into a suitable mammalian host cell for expression or coexpression using a number of viral based systems which have been developed for gene transfer into mammalian cells. For example, retroviruses provide a convenient platform for gene delivery systems. A selected nucleotide sequence encoding a $V_H$ and/or a $V_L$ domain polypeptide can be inserted into a vector and packaged in retroviral particles using techniques known in the art. The recombinant virus can then be isolated and delivered to a subject. A number of suitable retroviral systems have been described (U.S. Pat. No. 5,219,740; Miller and Rosman (1989) *BioTechniques* 7:980–990; Miller, A. D. (1990) *Human Gene Therapy* 1:5–14; Scarpa et al. (1991) *Virology* 180:849–852; Burns et al. (1993) *Proc. Natl. Acad. Sci. USA* 90:8033–8037; and Boris-Lawrie and Temin (1993) *Cur. Opin. Genet. Develop.* 3:102–109. Particularly preferred methods for producing and using retroviral vectors for gene therapy herein are described, for example, in International Publication No. WO 91/02805, published Mar. 7, 1991, and in U.S. patent application Ser. No.: 08/404,796, filed Mar. 15, 1995 for "Eukarotic Layered Vector Initiation System;" Ser. No. 08/405,627, filed Mar. 15, 1995 for "Recombinant α-Viral Vectors;" and Ser. No. 08/156,789, filed Nov. 23, 1993 for "Packaging Cells."

A number of suitable adenovirus vectors have also been described. Unlike retroviruses which integrate into the host genome, adenoviruses persist extrachromosomally thus minimizing the risks associated with insertional mutagenesis (Haj-Ahmad and Graham (1986) *J. Virol.* 57:267–274; Bett et al. (1993) *J. Virol.* 67:5911–5921; Mittereder et al. (1994) *Human Gene Therapy* 5:717–729; Seth et al. (1994) *J. Virol.* 68:933–940; Barr et al. (1994) *Gene Therapy* 1:51–58; Berkner, K. L. (1988) *BioTechniques* 6:616–629; and Rich et al. (1993) *Human Gene Therapy* 4:461–476).

Various adeno-associated virus (AAV) vector systems have been developed recently for gene delivery. Such systems can include control sequences, such as promoter and polyadenylation sites, as well as selectable markers or reporter genes, enhancer sequences, and other control elements which allow for the induction of transcription. AAV vectors can be readily constructed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988) *Molec. Cell. Biol.* 8:3988–3996; Vincent et al. (1990) *Vaccines* 90 (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; Kotin, R. M. (1994) *Human Gene Therapy* 5:793–801; Shelling and Smith (1994) *Gene Therapy* 1:165–169; and Zhou et al. (1994) *J. Exp. Med.* 179:1867–1875.

Additional viral vectors which will find use for delivering the present nucleic acid molecules encoding the Fab molecules include those derived from the pox family of viruses, including vaccinia virus and avian poxvirus. By way of example, vaccinia virus recombinants expressing the genes can be constructed as follows. The DNA encoding the particular Fab molecule is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the Fab molecule into the viral genome. The resulting TK⁻ recombinant can be selected by culturing the cells in the presence of 5-bromodeoxyuridine and picking viral plaques resistant thereto.

A vaccinia based infection/transfection system can be conveniently used to provide for inducible, transient expression of the Fab molecules in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, *Proc. Natl. Acad. Sci. USA* (1990) 87:6743–6747; Fuerst et al., *Proc. Natl. Acad. Sci. USA* (1986) 83:8122–8126.

Alternatively, avipoxviruses, such as the fowlpox and canarypox viruses, can also be used to deliver the Fab-encoding nucleotide sequences. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., the International Publications WO 91/12882; WO 89/03429, published Apr. 20, 1989; and WO 92/03545, published Mar. 5, 1992.

Molecular conjugate vectors, such as the adenovirus chimeric vectors described in Michael et al. *J. Biol. Chem.* (1993) 268:6866–6869 and Wagner et al. *Proc. Natl. Acad. Sci. USA* (1992) 89:6099–6103, can also be used for gene delivery under the invention.

Assay Reagents and Diagnostic Kits

The above-described anti-HCV binding molecules (the recombinant monoclonal antibodies, including Fab molecules, Fv fragments and sFv molecules) which are capable of reacting immunologically with samples containing HCV particles are also used herein to detect the presence of HCV viral particles and/or viral antigens in specific binding assays of biological samples. In particular, the novel specific binding molecules of the present invention can be used in highly sensitive methods for screening and identifying individuals carrying and/or infected with HCV, as well as for screening for HCV-contaminated blood or blood products. The present binding molecules can also be used in assays for monitoring the progress of anti-HCV therapies in treated individuals, and for monitoring the growth rate of HCV cultures used in research and investigation of the HCV agent.

The format of specific binding assays will be subject to a great deal of variation in accordance with procedures that are well known in the art. For example, specific binding assays can be formatted to utilize one, or a mixture of several, of the recombinant human monoclonal antibodies, (including Fab molecules, Fv fragments as well as sFv molecules) that have been prepared according to the present invention. The assay format can be generally based, for example, upon competition, direct binding reaction or sandwich-type assay techniques. Furthermore, the present assays can be conducted using immunoprecipitation or other techniques to separate assay reagents during, or after commencement of, the assay. Other assays can be conducted using specific binding molecules that have been insolubilized prior to commencement of the assay. In this regard, a number of in solubilization techniques are well known in the art, including, without limitation, in solubilization by adsorption to an immunosorbent or the like, absorption by contact with the wall of a reaction vessel, covalent crosslinking to insoluble matrices or "solid phase" substrates, non-covalent attachment to solid phase substrates using ionic or hydrophobic interactions, or by aggregation using precipitants such as polyethylene glycol or cross-linking agents such as glutaraldehyde.

There are a large number of solid phase substrates which can be selected for use in the present assays by those skilled in the art. For example, latex particles, microparticles, magnetic-, para-magnetic- or nonmagnetic-beads, membranes, plastic tubes, walls of microtitre wells, glass or silicon particles and sheep red blood cells all are suitable for use herein.

In general, most of the present assays involve the use of a labeled binding complex formed from the combination of a specific binding molecule (recombinant monoclonal antibodies, Fab fragments, Fv fragments and sFv molecules) with a detectable label moiety. A number of such labels are known in the art and can be readily attached (either using covalent or non-covalent association techniques) to the binding molecules of the present invention to provide a binding complex for use in the above-noted assay formats. Suitable detectable moieties include, but are not limited to, radioactive isotopes, fluorescers, luminescent compounds (e.g., fluorescein and rhodamine), chemiluminescers (e.g., acridinium, phenanthridinium and dioxetane compounds), enzymes (e.g., alkaline phosphatase, horseradish peroxidase and beta-galactosidase), enzyme substrates, enzyme cofactors, enzyme inhibitors, dyes, and metal ions. These labels can be associated with the binding molecules using attachment techniques that are known in the art.

Exemplary assay methods generally involve the steps of: (1) preparing the detectably labeled binding complexes as above; (2) obtaining a sample suspected of containing HCV particles and/or HCV antigen; (3) incubating the sample with the labeled complexes under conditions which allow for the formation of a specific binding molecule-antigen complex (e.g., an antibody-antigen complex); and (4) detecting the presence or absence of labeled binding molecule-antigen complexes. As will be appreciated by those skilled in the art upon the reading of this specification, such assays can be used to screen for the presence of HCV infection in human donor blood and serum products, for monitoring the growth rate of HCV cultures in diagnostic and/or research settings, for detecting HCV infection in an individual, or for monitoring the therapeutic effect of an anti-HCV treatment protocol in an infected subject. When the assays are used in the clinical setting, e.g., for detecting HCV infection or monitoring anti-HCV therapies, samples can be obtained from human and animal body fluids, such as whole blood, serum, plasma, cerebrospinal fluid, urine and the like. Furthermore, the assays can be readily used to provide quantitative information using reference to standards or calibrants as known in the art.

In one particular assay method of the invention, an enzyme-linked immunosorbent assay (ELISA) can be used to quantify an HCV antigen concentration in a sample. In the method, the specific binding molecules of the present invention are conjugated to an enzyme to provide a labeled binding complex, wherein the assay uses the bound enzyme as a quantitative label. In order to measure antigen, a binding molecule capable of specifically binding the selected HCV antigen (e.g., an antibody molecule) is immobilized to a solid phase substrate (e.g., a microtitre plate or plastic cup), incubated with test sample dilutions, washed and incubated with the binding molecule-enzyme complexes of the invention, and then washed again. In this regard, suitable enzyme labels are generally known, including, for example, horseradish peroxidase. Enzyme activity bound to the solid phase is measured by adding the specific enzyme substrate, and determining product formation or substrate utilization colorimetrically. The enzyme activity bound to the solid phase substrate is a direct function of the amount of antigen present in the sample.

In another particular assay method of the invention, the presence of HCV in a biological sample (e.g., as an indicator of HCV infection) can be detected using strip immunoblot assay (SIA) techniques, such as those known in the art which combine traditional Western and dot blotting techniques, e.g., the RIBA® (Chiron Corp., Emeryville, Calif.) test. In these assays, one or more of the specific binding molecules (the recombinant monoclonal antibodies, including Fab molecules) are immobilized as individual, discrete bands on a membranous support test strip. Visualization of reactivity with HCV particles present in the biological sample is accomplished using sandwich binding techniques with labeled antibody-conjugates in conjunction with a colorimetric enzyme substrate. Internal controls can also be present on the strip. The assay can be performed manually or used in an automated format.

Furthermore, the recombinant human monoclonal antibodies, (including Fab molecules, Fv fragments as well as sFv molecules) that have been prepared according to the present invention can be used in affinity chromatography techniques in order to detect the presence of HCV in a biological sample. Such methods are well known in the art.

Kits suitable for use in conducting any of the above-described assays and affinity chromatography techniques, and containing appropriate labeled binding molecule complex reagents can also be provided in accordance with the practice of the invention. Assay kits are assembled by packaging the appropriate materials, including all reagents and materials necessary for conducting the assay in a suitable container, along with an appropriate set of assay instructions.

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Experimental

EXAMPLE 1

Characterization of the Library Donor

Bone marrow was obtained from a 60 year old asymptomatic, male blood donor, who was found to be HCV positive during regular screening in conjunction with a blood donation. The cause of infection was unknown. The donor was unimmunized, and had received no treatment for the HCV infection prior to the bone marrow aspiration, which amounted to approximately 3 ml. The genotype of HCV in the donor's serum at the time of bone marrow donation was determined using a published method and found to be HCV 2b. Widell et al. (1994) *J Med Virol* 44:272–279.

In particular, the nucleotide sequence of the hypervariable region 1 (HVR1) of the E2 gene of the HCV isolate from the donor was obtained as follows. Single stranded template DNA was obtained, and a sequencing reaction was performed using newly designed primers (A. Widell et al, manuscript in preparation), in a cycle sequencing reaction with labelled nucleotides (PCR cycle sequencing kit, Perkin-Elmer) according to the manufacturers instructions. Allander et al. (1994) *J Med Virol* 43:415–419. The reaction product was run on an automated sequencer (Applied Biosystems, Calif.), and the data edited and analyzed using MacMolly software (available from SoftGene, Berlin, Germany). The deduced amino acid sequence of the HVR-E2 region of the donor isolate was determined to be as follows:
VAGVDASTYTTGGQSGRTTYGIVGLFS-LGPSQKLSLINTNGSWHINR [SEQ ID NO.: 17].

EXAMPLE 2

Construction of the Phage Display Library

Lymphocytes were isolated from the bone marrow sample obtained in Example 1 using Ficoll-Paque (Pharmacia Biotech, Uppsala, Sweden). Total RNA was extracted by the acid phenol extraction method (Chomczynski et al. (1987) *Anal Biochem* 162:156–159), first strand cDNA synthesis utilizing oligo-dT priming of 10 µg of RNA was performed (cDNA synthesis kit, Pharmacia Biotech) and heavy (Fd) and light chain DNA was PCR amplified using 5' biotinylated primers of previously published sequences for γ1 heavy and κ light chains (5' primers: VH1a, VH1f, VH2f, VH3a, VH3f, VH4f, VH6a, VH6f, Vk1a, Vk2a, Vk3a; 3'-primers: CG1z and CK1a) (available from Scandinavian Gene Synthesis, Köping, Sweden). See, e.g., Persson et al. (1991) *Proc Natl Acad Sci USA* 88:2432–2436, Kang et al. (1991) *Methods: Comp. Meth Enzymol* 2:111–118.

PCR was performed using a Thermal Cycler 4800 (Perkin-Elmer) at 94° C. for 5 minutes, then 35 cycles of 94° C. for 60 seconds, 52° C. for 30 seconds, and 72° C. for 180 seconds. After the 35 cycles, an extension step at 72° for 10 minutes completed the PCR procedure. PCR products were analyzed by running a fraction of each in a 1.5% agarose gel, the heavy and light chain DNA were pooled separately, phenol-chloroform extracted and then ethanol precipitated.

12 µg each of heavy and light chain DNA was gel purified on a 2.5% agarose gel, electroeluted (Schleicher & Schuell, Germany), and digested with the restriction endonucleases XhoI/SpeI, and SacI/XbaI, respectively (available from Life Technologies, Gaithersburg, Md.). The digested PCR products were subsequently gel purified, recovered by electroelution, and ligated into the vector pComb3H (Barbas, III et al. (1995) *Methods: Comp. Meth Enzymol* 8:94–103) after it had been digested with the corresponding restriction enzymes and gel purified/electroeluted as previously described for similar vector systems (Yang et al. (1995) *J Mol Biol* 254:392–403, Barbas, III et al. (1991) *Proc Natl Acad Sci USA* 88:7978–7982). For ligations, T4 ligase (Life Technologies) was used at 0.5 units per 10 µl reaction volume at approximately 16° C. over night. The combinatorial library was expressed on phage, including harvesting of phage, as reported. Samuelsson et al. (1995) *Virology* 207:495–502.

Ligation with light chain genes into pComb3H gave a library of 2×10$^7$ members. The subsequent ligation of Fd genes into this library resulted in a γ1/κ library with 2×10$^6$ members.

EXAMPLE 3

Preparation of the HCV E2 Selecting Antigens

A truncated, secreted form of the HCV E2 molecule was constructed which includes amino acids 383$_{ala}$ through 715$_{lys}$ (using the nomenclature of Choo et al. (1991) *Proc Natl Acad Sci USA* 88:2451–2455). The E2 molecule was expressed using a Chinese hamster ovary cell/dihydrofolate reductase (CHO/DHFR) expression system to provide a "conformational HCV E2 antigen" as follows. A DNA fragment of HCV E2 from amino acid 383 to amino acid 715 of HCV1 was generated by PCR and then ligated into a plasmid vector having the murine cytomegalovirus (MCMV) immediate early promoter/enhancer (Dorsch-Hasler et al. (1985) *Proc Natl Acad Sci USA* 82:8325–8329) and the selectable dhfr gene marker. The resultant plasmid was then stably transfected into dhfr⁻ CHO cells to generate a stable recombinant CHO cell line which secreted the conformational HCV E2 antigen.

The conformational E2 antigen was purified using known methods (Rosa et al. (1996) *Proc Natl Acad Sci USA* 93:1759–1763) as follows. Conditioned media from the CHO cells was concentrated 15-fold by ultrafiltration, followed by a further 10-fold volume reduction by ammonium sulfate precipitation at 75% saturation, and redissolution into 25 mM Tris chloride/1 mM EDTA, pH 7.5. The monoclonal antibody 5E5/H7 (raised against HeLa E1/E2) was used for purification. The antibody column was equilibrated in 25 mM Tris chloride/0.15 M NaCl, pH 7.5. The ammonium sulfate-precipitated E2 was dissolved in 25 mM Tris chloride/1 mM EDTA, pH 7.5, and loaded onto the column. The column was washed with phosphate buffered saline (PBS)/1 M NaCl and then eluted with 3–4 column volumes of Actisep (Sterogene, Arcadia, Calif.). All of the yellow-colored Actisep-containing fractions were pooled, concentrated in a stirred cell ultrafilter, and diafiltered into PBS buffer.

A recombinant HCV E1/E2 complex antigen was constructed and expressed using a Chinese hamster ovary cell/dihydrofolate reductase (CHO/DHFR) expression system as follows. Plasmid pMCMV-HC5p (Spaete et al. (1992) *Virology* 188:819–830) which encodes the HCV structural region as a 917 amino acid polypeptide spanning Met$_1$ to Gly$_{917}$ of the HCV1 genome was generated by cloning a 2813 base pair (bp) HCV StuI fragment from pGEM-4 blue-HC5p-1 8 into the unique SalI site of the mammalian cell expression vector pMCVAdhfr (Spaete et al. (1990) *J Virol* 64:2922–2931). The pMCVAdhfr vector encodes the selectable dhfr gene with transcription of the expressed gene driven by the MCMV immediate early promoter/enhancer and terminated by SV40 polyadenylation sequences. The Klenow fragment (Boehringer-Mannheim Biochemicals, Indianapolis, Ind.) was used to fill the SalI site prior to ligation of the StuI fragment. The pMCMV-HC5p plasmid was stably transfected into dhfr⁻ CHO cells to generate a stable recombinant CHO cell line (#62) which expresses the recombinant HCV E1/E2 complex antigen.

The recombinant E1/E2 complex antigen was purified using known methods (Choo et al. (1994) *Proc Natl Acad Sci USA* 91:1294–1298) as follows. CHO cell line #62 was harvested by pelleting and freezing. After lysis by Dounce homogenization in hypotonic buffer, the pellet was extracted by homogenizing in 2% Triton X-100®, and E1 (33 kD) and E2 (72 kD) were selectively copurified by successive chromatography on agarose-bound Gralanthus Nivalis-lectin (Vector Laboratories) and fast-flow S-Sepharose cation exchanger (Pharmacia).

EXAMPLE 4

Panning of the Combinatorial Library

Antigenic selection of specifically-binding Fab molecules was conducted using a variation on known techniques.

Burton et al. (1991) *Proc Natl Acad Sci USA* 88:10134–10137. In particular, four wells of a microtiter plate (Costar 3690, Cambridge, Mass.) were coated at 4° C. overnight with 50 μl of purified recombinant conformational HCV E2 antigen (prepared in Example 3), expressed in CHO cells, at 2.5 μg/ml. Spaete et al. (1992) *Virology* 188:819–830. Blocking was effected by completely filling the wells with 5% non-fat dry milk in PBS for 1 h at 22° C. 50 μl of the phage library ($5 \times 10^{10}$ cfu) was added to each well, and the plate was incubated for 2 hours at 37° C. Phage were removed and each well was washed by completely filling with a solution of PBS and 0.5% Tween 20 for 5 minutes, and then thoroughly removing the wash solution. Washing was performed 1–10 times as described below. Phage were eluted by adding 50 μl per well of elution buffer (0.1 M HCl adjusted to pH 2.2 with solid glycine) and incubating for 10 minutes at ambient temperature. The elution buffer was removed and neutralized with 3 μl of 2 M Tris base per 50 μl of elution buffer. *E. coli* XL-1 blue cells (Barbas, III et al. (1991) *Methods: Comp. Meth Enzymol* 2:119–124) were infected by the eluted phage, aliquots plated, and propagation of phase after each round of panning effected as has been described. Samuelsson et al. (1995) *Virology* 207:495–502.

In the first round of pannings (Panning Series I), the number of washings was increased for each panning, while in the second round of pannings (Panning Series II), a single panning with 10 washings was performed. As can be seen by the results depicted in Table I, a 100 fold increase in eluted phage was noted in Panning Series I.

TABLE I

| Panning No. | Washes (No.) | Eluted Phage (cfu) | Enrichment Factor |
|---|---|---|---|
| Panning Series I | | | |
| 1 | 1 | $2.6 \times 10^6$ | — |
| 2 | 3 | $2.6 \times 10^7$ | 9 |
| 3 | 10 | $2.6 \times 10^8$ | 100 |
| Panning Series II | | | |
| 1 | 10 | $2.4 \times 10^5$ | |

EXAMPLE 5

Expression of the Fab Molecules

Fab molecules were expressed by growing ampicillin resistant *E. coli* XL-1 blue cell colonies, containing Fab plasmids, with the gIII gene (encoding the cpIII anchor protein) (a) intact to provide insoluble Fab fragments, or (b) deleted by digestion with SpeI and NheI to provide soluble Fab fragments (digestion with these enzymes provides compatible cohesive ends; thus, the resulting DNA fragment lacking the gIII fragment can be gel-purified and self-ligated), in SB medium (super broth; 30 g tryptone, 20 g of yeast extract, and 10 g of MOPS per liter, pH 7) (Burton et al. (1991) *Proc Natl Acad Sci USA* 88:10134–10137) containing 50 μg/ml ampicillin and 1% glucose, until an $OD_{600nm}$ of about 1.0 was reached. The bacterial host cells were pelleted by centrifugation, and media exchanged to SB medium with 1 mM IPTG and 20 mM $MgCl_2$, and the cells resuspended. The resulting culture was incubated at room temperature on a shaker platform set at about 290 rpm and left overnight. The following day, cells were spun down, the supernatant discarded, PBS added (to between 2 to 4% of original culture volume) and the periplasmic contents of the bacterial cells released by three cycles of freeze-thawing. Bacterial debris was pelleted by centrifugation, and the Fab molecule-containing supernatant aliquoted to new vials. The Fab molecules were maintained at −20° C. until used.

EXAMPLE 6

Expression Levels of the Fab Clones

The expression levels of Fab molecules (obtained in Example 5) were ascertained using known ELISA techniques. Samuelsson et al. (1995) *Virology* 207:495–502. In particular, goat anti-human $F(ab')_2$ (Pierce, USA) or goat anti-human Fd (The Binding Site, UK) was diluted 1:1000 in 0.1 M carbonate-bicarbonate buffer, pH 9.6 and coated on microtiter wells by incubation overnight at 4° C. Coating solution was discarded, and the wells were blocked with 5% dry milk in PBS for 1 hr at ambient temperature, after which the blocking solution was removed, and Fab samples (from Example 5) at appropriate dilutions in PBS-T were added. After incubation at ambient temperature for 1 hour, the plates were washed, and ALP-goat anti human $F(ab')_2$ at a 1:500 dilution was added. After 1 hour incubation, and five subsequent washes, the label substrate solution, p-nitrophenylphosphate (Sigma, USA) in 0.1 M diethanolamine, pH 9.8 was added. Absorbance was measured at 405 nm in a microplate reader (Dynastar, Mass.). Most Fab clones were found to produce between 0.2 and 2.0 mg Fab/L culture, corresponding to 10–100 μg/ml in the periplasmic preparations. The expressed Fab clones were screened for E2 reactivity and promptly sequenced, in order to identify multiple copies of the same original clone.

EXAMPLE 7

Western Blot for Heavy and Light Chain Expression

In order to test for correct expression of both chains, several Fab molecules were analyzed in Western blots using antiserum for human Fd- and light chains. In particular, 10 μl of the periplasmic Fab molecule preparations (prepared in Example 5) were separated on a precast 12% Tris-glycine polyacrylamide gel, and transferred to a nitrocellulose membrane by electroblotting using an Xcell Mini-cell apparatus (Novex Experimental Technology, San Diego, Calif.). The membrane was blocked in 5% dry milk over night, and incubated with either alkaline phosphatase coupled anti-human Fab antiserum (available from Pierce) diluted 1:1000 in 5% dry milk and 0.05% Tween 20 (PBS-MT) for 3 h at 22° C. during constant rocking. The subject anti-human Fab antiserum was chosen since it is known to be mainly reactive to light chains. To detect the heavy (Fd) chain expression products, strips were first incubated with a sheep-anti-human Fd serum (Binding Site, U.K.) which was diluted to 1:1000 and incubated (as above), washed and then incubated again with a secondary antibody, AP-anti-goat IgG (Sigma, St. Louis, Mo.) at a dilution of 1:500.

Following the last incubation for 1 hour at 22° C., the membranes were washed three times in PBS-T, and color development was performed with 2 ml BCIP/NBT solution (Sigma, St Louis, Mo.) for 7 minutes. Membranes were rinsed in water and dried. Prestained molecular weight markers (Amersham, U.K.) were used in each blot.

For all clones tested, expression of both chains was approximately equivalent. The heavy chain (expressed as a fusion polypeptide with the truncated gIII protein) showed an approximate molecular weight of 70 kD.

EXAMPLE 8

Sequencing of the Fab Clones

Plasmid DNA from each Fab molecule clone grown in the E. coli XL-1 blue cell cultures (in Example 5), was isolated using a Wizard mini prep DNA purification reagent system (Promega). Single stranded DNA was obtained by PCR, using primers that hybridized upstream and downstream of the cloning regions in the pComb3H vector (pC3H-2488S: 5'-CAA CGC AAT TAA TGT GAG TTA G [SEQ ID NO.: 18]; G-back: 5'-GCC CCC TTA TTA GCG TTT GCC ATC [SEQ ID NO.: 19]). In each reaction, one of the two PCR primers used was biotinylated at the 5' terminus. After 35 cycles of PCR amplification, single stranded DNA was obtained by denaturing the DNA under alkaline conditions and absorbing the biotinylated DNA strand to streptavidin coated beads (Dynal, Oslo, Norway) using known techniques. Hultman et al. (1989) *Nucl Acid Res* 17:4937–4945. Dideoxy sequencing reactions according to the method of Sanger et al. (1977) *Proc Natl Acad Sci USA* 74:5463–5467 was performed utilizing FITC-labelled primers hybridizing 3' of the junction between the variable and constant Ig regions (SEQKb: 5'-ATA GAA GTT GTT CAG CAG GCA [SEQ ID NO.: 20] for the κ light chains, and SEQGb: 5'-GTC GTT GAC CAG GCA GCC CAG [SEQ ID NO.: 21] for γ heavy chains); or 5' to the start of the heavy and light chain genes, respectively (omp-seq: 5'-AAG ACA GCT ATC GCG ATT GCA G [SEQ ID NO.: 22]; pel-seq: 5'-ACC TAT TGC CTA CGG CAG CCG [SEQ ID NO.: 23]). The reaction products were run on an automated sequencer (A.L.F., Pharmacia Biotech), and were translated and aligned using the MacMolly software (SoftGene, Berlin, Germany).

From the first round of pannings conducted in Example 4 (Panning Series I), 10 Fab molecule clones (identified as Fab molecule clones L1–L10) that were assayed for expression (as described in Examples 6 and 7) were sequenced using the above-described sequencing method, and found to have very similar CDR3 sequences in their heavy chains (the H3 region), indicating that they all derived from the same B-cell clone. Litwin et al. (1990) *J Exp Med* 171:293–297. However, while the VDJ junctions and the length of the H3 regions were identical, a number of different point mutations were identified in their heavy chains, and each heavy chain was combined with a different light chain. One clone, identified as Fab molecule clone L3, was selected for further testing.

From the second round of pannings conducted in Example 4 (Panning Series II), 20 Fab molecule clones (identified as Fab molecule clones 1:1–1:20) that were assayed for expression (as described in Examples 6 and 7) were sequenced using the above-described sequencing method. From this round of sequencing, 6 Fab clones were found to produce insufficient levels of Fab, and 4 Fab clones were found to exhibit cross reactivity to control antigen in a specific binding assay. From the sequencing information obtained from the remaining 10 Fab clones, it was found that 7 Fab clones carried heavy chains related to the ones found in the Panning Series I (the L1–10 Fab molecule clones). However, 3 of the 7 Fab clones had distinctly different H3 regions from the Panning Series I clones, and were also unique relative to each other. These clones were identified herein as Fab molecule clones 1:5, 1:7, 1:11.

The κ light chain nucleic acid sequences of the Fab molecule clones 1:5 [SEQ ID NO.: 9], 1:7 [SEQ ID NO.: 10], 1:11 [SEQ ID NO.: 11], and L3 [SEQ ID NO.: 12] are depicted in FIGS. 3A–3D, respectively. The γ1 heavy chain nucleic acid sequences of the Fab molecule clones 1:5 [SEQ ID NO.: 13], 1:7 [SEQ ID NO.: 14], 1:11 [SEQ ID NO.: 15], and L3 [SEQ ID NO.: 16] are depicted in FIGS. 4A–4D, respectively.

The deduced γ1 heavy chain amino acid sequences of the Fab molecule clones 1:5 [SEQ ID NO.: 1], 1:7 [SEQ ID NO.: 2], 1:11 [SEQ ID NO.: 3], and L3 [SEQ ID NO.: 4] are depicted in FIGS. 1A–1D, respectively. The CDR regions (CDR1, CDR2 and CDR3) from each chain have been identified in the Figures.

The deduced κ light chain amino acid sequences of the Fab molecule clones 1:5 [SEQ ID NO.: 5], 1:7 [SEQ ID NO.: 6], 1:11 [SEQ ID NO.: 7], and L3 [SEQ ID NO.: 8] are depicted in FIGS. 2A–2D, respectively. The CDR regions (CDR1, CDR2 and CDR3) from each chain have also been identified as noted above.

EXAMPLE 9

ELISA Assay for HCV E2 Antigen Reactivity

The Fab molecule clones 1:5, 1:7, 1:11 and L3 were screened for HCV E2 antigen reactivity as follows. Either recombinant conformational HCV E2 antigen, or recombinant HCV E1/E2 complex antigen (prepared in Example 3) was diluted to 0.25 μg/ml in 0.05 M carbonate-bicarbonate buffer, pH 9.6, and coated to microtitre wells (Costar #3690; Life Technologies) overnight at 4° C. Unbound antigen was discarded, and the wells were blocked with 5% nonfat dry milk in PBS for 60 minutes at ambient temperature. After the blocking solution was discarded, solutions containing the Fab molecules to be tested were added at 1:2, 1:10 and 1:100 dilutions (diluent: PBS with 0.1% NP-40). The plates were incubated at ambient temperature for 2 hours, washed five times with PBS with 0.05% Tween 20 (PBS-T), and ALP-goat anti-human F(ab')$_2$ (Pierce, Rocherford, Ill.) was added at a 1:1000 dilution. After 60 minutes and subsequent washes, substrate solution (p-nitrophenylphosphate) (SIGMA, St. Louis, Mo.) was added and absorbance was measured at 405 nm in a microplate reader (Dynastar, Mass.).

The cut-off value for positive readings was set at 4 times the OD value obtained for a negative control sample which comprised an anti-HIV Fab of equal concentrations. Barbas III et al. (1991) *Proc Natl Acad Sci USA* 88:7978–7982. For control purposes, bovine serum albumin (BSA) (SIGMA), HIV gp120$_{LAI}$ (Intracell, Cambridge, Mass.) and tetanus toxoid (TT) (SBL Vaccin, Solna, Sweden) coated at 5, 1, and 1 μg/ml, respectively, were used in corresponding ELISAs as controls for unspecific reactivity.

The results from the ELISAs are depicted in Table II below. As can be seen, Fab molecules expressed from the 1:5, 1:7, 1:11 and L3 clones each reacted strongly with both the conformational HCV E2 antigen and the HCV E1/E2 complex antigen, while showing no cross reaction with the control antigens (BSA, HIVgp120 and TT).

TABLE II

| Clone | [Fab] (μg/ml)[1] | E2[2] | E1/E2[2] | BSA[2] | HIV gp120[2] | TT[2] |
|---|---|---|---|---|---|---|
| L 3 | 100 | 1.695 | 2.460 | 0.089 | ND | 0.313 |
| 1:5 | 10 | 0.219 | 0.614 | 0.031 | ND | 0.012[3] |

TABLE II-continued

| Clone | [Fab] (μg/ml)[1] | E2[2] | E1/E2[2] | BSA[2] | HIV gp120[2] | TT[2] |
|---|---|---|---|---|---|---|
| 1:7 | 100 | >3.000 | >3.000 | 0.006 | ND | ND |
| 1:11 | 10 | >3.000 | 1.831 | 0.506 | ND | ND |

[1]Fab concentration in the periplasmic preparation used in the analyses.
[2]OD$_{405}$ nm, sample diluted 1:10.
[3]sample diluted 1:100.

EXAMPLE 10

Western Blot Assay for HCV E2 Antigen Reactivity

The Fab molecule clones 1:5, 1:7, 1:11 and L3 were screened for HCV E2 antigen reactivity using the following techniques. Western blots were conducted using 1 μg of the recombinant conformational HCV E2 glycoprotein (obtained in Example 3) that was denatured by heating to 98° C. for 5 min in a Laemmli buffer, separated on a 8–16% polyacrylamide gradient gel (Novex Experimental Technologies), and transferred to a nitrocellulose membrane that was blocked as described above, and cut into strips. Subsequently, each strip was incubated with an Fab preparation (expressed from the 1:5, 1:7, 1:11 and L3 clones) that was diluted 1:20 in PBS-MT for 2 hours at 22° C. with constant rocking. The strips were washed three times in PBS-T, and alkaline phosphatase conjugated goat anti-human Fab serum (Pierce), diluted 1:1000 in PBS-MT, was added. Following incubation for 1 hour at 22° C., the strips were again washed three times in PBS with 0.05% Tween 20, and color development was performed with 2 ml BCIP/NBT solution (Sigma, St Louis, Mo.) for 10 minutes. As a positive control, a human anti-HCV positive serum was incubated with one strip instead of the Fab preparations.

None of the tested Fab molecules (from clones 1:5, 1:7, 1:11 and L3) reacted to the denatured HCV E2 antigen in the Western blot, indicating that each Fab molecule binds to a conformational epitope of the HCV E2 antigen.

EXAMPLE 11

Inhibition ELISA Assay for Affinity Determination

The affinity of the Fab molecules (from clones 1:5, 1:7, 1:11 and L3) for HCV E2 antigen was estimated using an inhibition ELISA method as previously described. Persson et al. (1991) Proc Natl Acad Sci USA 88:2432–2436, Rath et al. (1988) J Immun Methods 106:245–249. Samples to be tested were first titred at ten-fold dilutions in order to bracket a concentration where a ten-fold reduced concentration gave a substantial reduction in detected binding in the HCV E2 ELISA. For affinity measurements, coating of microtitre wells with HCV E2 antigen and subsequent blocking was done as described above for the ELISA conducted in Example 9. Appropriate dilutions of the Fab samples, with or without added soluble HCV E2 antigen (final concentration 5 μg/ml) were added to the wells, and incubated at ambient temperature for 3 hours. The plates were washed uniformly 4 times with PBS-T, and developed using AP-anti Fab, substrate, and spectrophotometer reader as described above in Example 9. The reduction of OD in the presence of soluble HCV E2 antigen was calculated and the concentration needed for a 50% reduction estimated by extrapolation.

As depicted in Table III below, the approximate affinities of the Fab molecules (from clones 1:5, 1:7, 1:11 and L3) for the recombinant conformational HCV E2 antigen, varied between <1.7×10$^7$ to 3.0×10$^8$ M$^{-1}$.

TABLE III

| Clone | [Fab] (μg/ml) | K$_d$[1] (nM) | Affinity (M$^{-1}$) |
|---|---|---|---|
| L 3 | 1 | 14 | 7 × 10$^7$ |
| 1:5 | 5 | >56 | <1.7 × 10$^7$ |
| 1:7 | 1 | 3 | 3 × 10$^8$ |
| 1:11 | 0.1 | 14 | 7 × 10$^7$ |

[1]Approximate concentration needed of soluble E2 for 50% reduction in OD.

EXAMPLE 12

Inhibition of HCV E2 Binding

The ability of the Fab molecules (from clones 1:5, 1:7, 1:11 and L3) to block the binding of HCV E2 to target cells was determined using the method of Rosa et al. (1996) Proc Natl Acad Sci USA 93:1759–1763. In particular, the purified conformational HCV E2 antigen (prepared in Example 3) was used in indirect immunofluorescence experiments to assess the ability of the Fab molecules to neutralize binding of the HCV E2 polypeptide to human cells in vitro. MOLT-4 cells, a human cell line reported to allow low-level HCV replication in vitro (Shimizu et al. (1992) Proc Natl Acad Sci USA 89:5477–5481), were incubated at 4° C. with the conformational HCV E2 antigen, and subsequently incubated with serial dilutions of the Fab molecules. After incubation with fluorescein isothiocyanate-conjugated rabbit-anti-human IgG antiserum, binding of the conformational HCV antigen to the MOLT-4 cells was indirectly detected by flow cytometry as cell-bound fluorescence.

As can be seen in the results depicted in FIG. 5, Fab molecules from each of the 1:5, 1:7, 1:11 and L3 clones were able to block the binding of HCV E2 to the cells. Since the first contact between the HCV virus and its host occurs via binding of the virus envelope to cell-surface receptors, the ability of the present Fab molecules to neutralize this interaction establishes the effectiveness of using the present molecules in vaccinations to provide passive immunization to HCV.

Thus, novel human monoclonal antibodies to HCV E2 antigen are disclosed. Although preferred embodiments of the subject invention have been described in some detail, it is understood that obvious variations can be made without departing from the spirit and the scope of the invention as defined by the appended claims.

---

What is claimed is:

1. A recombinant human monoclonal antibody that exhibits immunological binding affinity for a hepatitis C virus (HCV) E2 antigen, wherein the antibody comprises a Fab molecule that comprises an HCV E2 antigen binding portion of a human γ1 heavy chain variable region ($V_H$) and an HCV E2 antigen binding portion of a human κ light chain variable region ($V_L$), and further wherein the $V_H$ region is selected from the group consisting of the contiguous sequence of amino acids depicted in FIG. 1A (SEQ ID NO: 1) or a contiguous sequence of amino acids with at least 90% sequence identity thereto, the contiguous sequence of amino acids depicted in FIG. 1B (SEQ ID NO: 2) or a contiguous sequence of amino acids with at least 90% sequence identity thereto, the contiguous sequence of amino acids depicted in FIG. 1C (SEQ ID NO: 3) or a contiguous sequence of amino acids with at least 90% sequence identity thereto, and the contiguous sequence of amino acids depicted in FIG. 1D (SEQ ID NO: 4) or a contiguous sequence of amino acids with at least 90% sequence identity thereto, and/or the $V_L$ region is selected from the group consisting of the contiguous sequence of amino acids depicted in FIG. 2A (SEQ ID NO: 5) or a contiguous sequence of amino acids with at least 90% sequence identity thereto, the contiguous sequence of amino acids depicted in FIG. 2B (SEQ ID NO: 6) or a contiguous sequence of amino acids with at least 90% sequence identity thereto, the contiguous sequence of amino acids depicted in FIG. 2C (SEQ ID NO: 7) or a contiguous sequence of amino acids with at least 90% sequence identity thereto, and the contiguous sequence of amino acids depicted in FIG. 2D (SEQ ID NO: 8) or a contiguous sequence of amino acids with at least 90% sequence identity thereto.

2. The monoclonal antibody of claim 1, wherein the Fab molecule comprises the heavy chain variable region ($V_H$) amino acid sequence depicted in FIG. 1A (SEQ ID NO:1).

3. The monoclonal antibody of claim 1, wherein the Fab molecule comprises the heavy chain variable region ($V_H$) amino acid sequence depicted in FIG. 1B (SEQ ID NO:2).

4. The monoclonal antibody of claim 1, wherein the Fab molecule comprises the heavy chain variable region ($V_H$) amino acid sequence depicted in FIG. 1C (SEQ ID NO:3).

5. The monoclonal antibody of claim 1, wherein the Fab molecule comprises the heavy chain variable region ($V_H$) amino acid sequence depicted in FIG. 1D (SEQ ID NO:4).

6. The monoclonal antibody of claim 1, wherein the Fab molecule comprises the light chain variable region ($V_L$) amino acid sequence depicted in FIG. 2A (SEQ ID NO:5).

7. The monoclonal antibody of claim 1, wherein the Fab molecule comprises the light chain variable region ($V_L$) amino acid sequence depicted in FIG. 2B (SEQ ID NO:6).

8. The monoclonal antibody of claim 1, wherein the Fab molecule comprises the light chain variable region ($V_L$) amino acid sequence depicted in FIG. 2C (SEQ ID NO:7).

9. The monoclonal antibody of claim 1, wherein the Fab molecule comprises the light chain variable region ($V_L$) amino acid sequence depicted in FIG. 2D (SEQ ID NO:8).

10. The monoclonal antibody of claim 1, further characterized in that said monoclonal antibody has a binding affinity of at least about $1.0 \times 10^7$.

11. The monoclonal antibody of claim 10, further characterized in that said monoclonal antibody also binds to the hepatitis C virus (HCV) E1/E2 complex as determined by an ELISA assay.

12. The monoclonal antibody of claim 1, wherein said monoclonal antibody comprises a F(ab')$_2$ fragment capable of binding to a hepatitis C virus (HCV) E2 antigen.

13. The monoclonal antibody of claim 1, wherein said monoclonal antibody consists essentially of a Fab molecule capable of binding to a hepatitis C virus (HCV) E2 antigen.

14. The monoclonal antibody of claim 13, further characterized in that said monoclonal antibody has a binding affinity of at least about $1.0 \times 10^7$.

15. The monoclonal antibody of claim 14, further characterized in that said monoclonal antibody also binds to a hepatitis C virus (HCV) E1/E2 complex as determined by an ELISA assay.

16. A composition comprising the monoclonal antibody of claim 1 and an acceptable vehicle.

17. The monoclonal antibody of claim 1, wherein the Fab molecule comprises the contiguous sequence of amino acids depicted in FIG. 1A (SEQ ID NO: 1) and the contiguous sequence of amino acids depicted in FIG. 2A (SEQ ID NO: 5).

18. The monoclonal antibody of claim 1, wherein the Fab molecule comprises the contiguous sequence of amino acids depicted in FIG. 1B (SEQ ID NO: 2) and the contiguous sequence of amino acids depicted in FIG. 2B (SEQ ID NO: 6).

19. The monoclonal antibody of claim 1, wherein the Fab molecule comprises the contiguous sequence of amino acids depicted in FIG. 1C (SEQ ID NO: 3) and the contiguous sequence of amino acids depicted in FIG. 2C (SEQ ID NO: 7).

20. The monoclonal antibody of claim 1, wherein the Fab molecule comprises the contiguous sequence of amino acids depicted in FIG. 1D (SEQ ID NO: 4) and the contiguous sequence of amino acids depicted in FIG. 2D (SEQ ID NO: 8).

21. A recombinant human monoclonal antibody that exhibits immunological binding affinity for a hepatitis C virus (HCV) E2 antigen, wherein the antibody comprises at least one group of three complementarity determining regions (CDRs) interposed between framework regions (FRs) said FRs derived from a human immunoglobulin, wherein the group of three CDRs is selected from the group consisting of amino acid residue numbers 32–36, 51–71, 104–121 of SEQ ID NO:1; amino acid residue numbers 32–36, 51–67, 100–116 of SEQ ID NO:2; amino acid residue numbers 32–36, 51–67, 100–117 of SEQ ID NO:3; amino acid residue numbers 31–35, 50–66, 99–114 of SEQ ID NO:4; amino acid residue numbers 23–34, 49–56, 89–97 of SEQ ID NO:5; amino acid residue numbers 23–33, 49–55, 88–95 of SEQ ID NO:6; amino acid residue numbers 23–34, 50–56, 89–97 of SEQ ID NO:7; and amino acid residue numbers 23–33, 49–55, 88–96 of SEQ ID NO:8.

22. The recombinant human monoclonal antibody of claim 21, wherein the antibody comprises a first group of CDRs with amino acid residue numbers 32–36, 51–71, 104–121 of SEQ ID NO:1 interposed between FRs, and a second group of CDRs with amino acid residue numbers 23–34, 49–56, 89–97 of SEQ ID NO:5, interposed between FRs, wherein the first and second groups of CDRs interposed between FRs together form a binding site for an HCV E2 antigen.

23. The recombinant human monoclonal antibody of claim 21, wherein the antibody comprises a first group of CDRs with amino acid residue numbers 32–36, 51–67, 100–116 of SEQ ID NO:2 interposed between FRs, and a second group of CDRs with amino acid residue numbers 23–33, 49–55, 88–95 of SEQ ID NO:6, interposed between FRs, wherein the first and second groups of CDRs interposed between FRs together form a binding site for an HCV E2 antigen.

24. The recombinant human monoclonal antibody of claim 21, wherein the antibody comprises a first group of CDRs with amino acid residue numbers 32–36, 51–67, 100–117 of SEQ ID NO:3 interposed between FRs, and a second group of CDRs with amino acid residue numbers amino acid residue numbers 23–34, 50–56, 89–97 of SEQ ID NO:7 interposed between FRs, wherein the first and second groups of CDRs interposed between FRs together form a binding site for an HCV E2 antigen.

25. The recombinant human monoclonal antibody of claim 21, wherein the antibody comprises a first group of CDRs with amino acid residue numbers amino acid residue numbers 31–35, 50–66, 99–114 of SEQ ID NO:4 interposed between FRs, and a second group of CDRs with amino acid residue numbers 23–33, 49–55, 88–96 of SEQ ID NO:8 interposed between FRs, wherein the first and second groups of CDRs interposed between FRs together form a binding site for an HCV E2 antigen.

26. A composition comprising the monoclonal antibody of claim 20 and an acceptable vehicle.

27. A composition comprising the monoclonal antibody of claim 20 and an acceptable vehicle.

28. A binding complex, comprising the monoclonal antibody of claim 20 and a detectable moiety attached thereto.

29. A binding complex, comprising the monoclonal antibody of claim 21 and a detectable moiety attached thereto.

30. A composition comprising the monoclonal antibody of claim 17 and an acceptable vehicle.

31. A composition comprising the monoclonal antibody of claim 18 and an acceptable vehicle.

32. A composition comprising the monoclonal antibody of claim 19 and an acceptable vehicle.

33. A binding complex, comprising the monoclonal antibody of claim 1 and a detectable moiety attached thereto.

34. A binding complex, comprising the monoclonal antibody of claim 17 and a detectable moiety attached thereto.

35. A binding complex, comprising the monoclonal antibody of claim 18 and a detectable moiety attached thereto.

36. A binding complex, comprising the monoclonal antibody of claim 19 and a detectable moiety attached thereto.

37. The binding complex of claim 33, wherein the detectable moiety is selected from the group consisting of radioactive isotopes, fluorescers, chemiluminescers, enzymes, enzyme substrates, enzyme cofactors, enzyme inhibitors and dyes.

38. The binding complex of claim 29, wherein the detectable moiety is selected from the group consisting of radioactive isotopes, fluorescers, chemiluminescers, enzymes, enzyme substrates, enzyme cofactors, enzyme inhibitors and dyes.

39. A method for detecting the presence of HCV particles in a sample suspected of containing HCV, comprising:
  (a) incubating the sample with the binding complex of claim 37, wherein the incubating is conducted under conditions which allow for formation of an antibody-antigen complex; and
  (b) detecting the presence or absence of the antibody-antigen complex.

40. A method for detecting the presence of HCV particles in a sample suspected of containing HCV, comprising:
  (a) incubating the sample with the binding complex of claim 38, wherein the incubating is conducted under conditions which allow for formation of an antibody-antigen complex; and
  (b) detecting the presence or absence of the antibody-antigen complex.

41. A method for monitoring the progress of an anti-HCV therapeutic treatment of a HCV-infected mammalian subject, comprising:
  (a) obtaining a biological sample from said subject;
  (b) incubating the sample with the binding complex of claim 37, wherein the incubating is conducted under conditions which allow for formation of an antibody-antigen complex; and
  (c) detecting the presence or absence of the antibody-antigen complex.

42. A method for monitoring the progress of an anti-HCV therapeutic treatment of a HCV-infected mammalian subject, comprising:
  (a) obtaining a biological sample from said subject;
  (b) incubating the sample with the binding complex of claim 38, wherein the incubating is conducted under conditions which allow for formation of an antibody-antigen complex; and
  (c) detecting the presence or absence of the antibody-antigen complex.

43. A composition comprising the monoclonal antibody of claim 22 and an acceptable vehicle.

44. A composition comprising the monoclonal antibody of claim 23 and an acceptable vehicle.

45. A composition comprising the monoclonal antibody of claim 24 and an acceptable vehicle.

46. A composition comprising the monoclonal antibody of claim 25 and an acceptable vehicle.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
       (A) LENGTH: 132 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:1:

```
Glu Val Gln Leu Leu Glu Gln Ser Gly Ala Glu Val Arg Lys Pro Gly
1               5                   10                  15

Ser Ser Val Lys Val Ser Cys Lys Ala Ser Gly Gly Thr Phe Ser Gly
            20                  25                  30

His Val Ile Thr Trp Val Arg Gln Ala Pro Gly Gln Gly Leu Glu Trp
        35                  40                  45

Met Gly Glu Ser Ile Pro Ile Phe Gly Ser Ala Asn Tyr Ala Gln Asn
    50                  55                  60

Tyr Ala Gln Lys Phe Arg Asp Arg Val Ser Ile Ile Ala Asp Glu Ser
65                  70                  75                  80

Thr Ser Thr Ser Phe Ile Glu Leu Ser Asn Leu Arg Ser Asp Asp Thr
                85                  90                  95

Ala Val Tyr Tyr Cys Ala Arg Asp Pro Pro Arg Tyr Cys Ser Ala Gly
            100                 105                 110

Arg Cys Tyr Pro Gly Phe Phe Gln Gln Trp Gly Gln Gly Thr Leu Val
        115                 120                 125

Thr Val Ser Ser
130
```

(2) INFORMATION FOR SEQ ID NO:2:

(i) SEQUENCE CHARACTERISTICS:
       (A) LENGTH: 127 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:2:

```
Glu Val Gln Leu Leu Glu Gln Ser Gly Ala Glu Val Lys Lys Pro Gly
1               5                   10                  15

Ser Ser Val Lys Val Ser Cys Gln Val Phe Gly Asp Thr Phe Ser Arg
            20                  25                  30

Tyr Thr Ile Gln Trp Leu Arg Gln Ala Pro Gly Gln Gly Pro Glu Trp
        35                  40                  45

Met Gly Asn Ile Ile Pro Val Tyr Asn Thr Pro Asn Tyr Ala Gln Lys
    50                  55                  60

Phe Gln Gly Arg Leu Ser Ile Thr Ala Asp Asp Ser Thr Ser Thr Ala
65                  70                  75                  80

Tyr Met Glu Leu Ser Ser Leu Arg Ser Glu Asp Thr Ala Val Tyr Phe
                85                  90                  95

Cys Ala Arg Val Val Ile Pro Asn Ala Ile Arg His Thr Met Gly Tyr
```

```
                       100                 105                 110
Tyr Phe Asp Tyr Trp Gly Gln Gly Thr Leu Val Thr Val Ser Ser
                 115                 120                 125

(2) INFORMATION FOR SEQ ID NO:3:

(i) SEQUENCE CHARACTERISTICS:
        (A) LENGTH: 128 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Glu Val Gln Leu Leu Glu Gln Ser Gly Ala Glu Val Lys Lys Pro Gly
1               5                   10                  15

Ser Ser Val Lys Val Ser Cys Lys Ala Ser Gly Gly Thr Phe Ser Gly
            20                  25                  30

His Val Ile Ser Trp Val Arg Gln Ala Pro Gly Gln Gly Leu Glu Trp
        35                  40                  45

Met Gly Gly Ser Ile Ser Phe Phe Gly Thr Ser Asn Ser Ala Gln Lys
    50                  55                  60

Phe Gln Gly Arg Val Ser Ile Thr Ala Asp Glu Ser Ala Ser Thr Ala
65                  70                  75                  80

Tyr Met Glu Leu Ser Ser Leu Arg Ser Glu Asp Thr Ala Ile Tyr Tyr
                85                  90                  95

Cys Ala Lys Asp Pro Pro Arg Phe Cys Ser Gly Gly Asn Cys Tyr Pro
            100                 105                 110

Gly Phe Phe Gln Gln Trp Gly Gln Gly Thr Leu Val Thr Val Ser Ser
        115                 120                 125

(2) INFORMATION FOR SEQ ID NO:4:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Lys Thr Tyr
            20                  25                  30

Gly Met His Trp Val Arg Gln Ala Pro Gly Lys Gly Leu Glu Trp Val
        35                  40                  45

Ala Gly Ile Ser Phe Asp Gly Ser Asn Gln Tyr Tyr Ala Asp Ser Val
    50                  55                  60

Lys Gly Arg Phe Ile Val Ser Arg Asp Asn Ser Arg Asp Thr Val Phe
65                  70                  75                  80

Leu Gln Met Ser Ser Leu Arg Leu Glu Asp Thr Ala Val Tyr Tyr Cys
                85                  90                  95

Ala Thr Glu Gly Ser Pro Phe Gly Ser Ile Lys Gly Arg Tyr Tyr Leu
            100                 105                 110

Glu Asn Trp Gly Gln Gly Thr Leu Val Thr Val Ser Ser
        115                 120                 125
```

(2) INFORMATION FOR SEQ ID NO:5:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Ala Glu Leu Thr Gln Ser Pro Gly Thr Leu Ser Leu Ser Pro Gly Glu
1               5                   10                  15

Arg Ala Thr Leu Ser Cys Arg Ala Ser Gln Ser Val Ser Ser Asn Tyr
                20                  25                  30

Leu Ala Trp Tyr Gln Gln Arg Pro Gly Gln Ala Pro Arg Leu Leu Ile
            35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Leu Tyr Gly Asn Ser Arg Trp
                85                  90                  95

Thr Phe Gly Gln Gly Thr Lys Val Glu Ile Lys
                100                 105

(2) INFORMATION FOR SEQ ID NO:6:

(i) SEQUENCE CHARACTERISTICS:
        (A) LENGTH: 105 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Ala Glu Leu Thr Gln Ser Pro Ala Thr Leu Ser Leu Ser Pro Gly Glu
1               5                   10                  15

Arg Ala Thr Leu Ser Cys Arg Ala Ser Gln Ser Val Asn Lys Tyr Leu
                20                  25                  30

Ala Trp Tyr Gln Gln Lys Pro Gly Gln Ala Pro Arg Leu Leu Ile Tyr
            35                  40                  45

Asp Ala Ser Asn Arg Ala Thr Gly Ile Pro Ala Arg Phe Ser Gly Ser
    50                  55                  60

Gly Ser Gly Thr Asp Phe Thr Leu Thr Ile Ser Asn Leu Glu Pro Glu
65                  70                  75                  80

Asp Phe Ala Val Tyr Tyr Cys Gln Gln Arg Ser Asp Trp Val Thr Phe
                85                  90                  95

Gly Gly Gly Thr Lys Val Glu Ile Lys
                100                 105

(2) INFORMATION FOR SEQ ID NO:7:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Ala Glu Leu Thr Gln Ser Pro Gly Thr Leu Ser Leu Ser Pro Gly Glu
1               5                   10                  15

Arg Ala Thr Leu Ser Cys Gly Ala Ser Gln Ser Val Arg Ser Asn Tyr
            20                  25                  30

Leu Ala Trp Tyr Gln Gln Lys Pro Gly Gln Ala Pro Arg Leu Leu Ile
            35                  40                  45

Tyr Gly Val Ser Ser Arg Ala Thr Gly Ile Pro Asp Arg Phe Ser Gly
50                      55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Arg
                85                  90                  95

Thr Phe Gly Gln Gly Thr Lys Leu Glu Ile Lys
                100                 105

(2) INFORMATION FOR SEQ ID NO:8:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Ala Glu Leu Thr Gln Ser Pro Ala Thr Leu Ser Val Ser Pro Gly Glu
1               5                   10                  15

Arg Ala Ser Leu Ser Cys Arg Ala Ser Gln Ser Val Gly Asn Asn Leu
            20                  25                  30

Ala Trp Tyr Gln Gln Lys Pro Gly Gln Ala Pro Arg Leu Leu Ile Tyr
        35                  40                  45

Gly Gly Asn Thr Arg Ala Thr Gly Thr Pro Asp Arg Phe Ser Gly Ser
50                  55                      60

Gly Ser Gly Thr Glu Phe Thr Leu Thr Ile Ser Ser Leu Gln Ser Glu
65              70                  75                  80

Asp Phe Ala Val Tyr Phe Cys Gln His Tyr Ser Thr Trp Pro Leu Thr
                85                  90                  95

Phe Gly Gly Gly Thr Lys Val Glu Phe Lys
                100                 105

(2) INFORMATION FOR SEQ ID NO:9:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GAGCTCACGC AGTCTCCAGG CACCCTGTCT TTGTCTCCAG GGGAAAGAGC CACCCTCTCC    60

TGCAGGGCCA GTCAGAGTGT TAGCAGCAAT TACTTAGCCT GGTACCAGCA GAGACCTGGC   120

CAGGCTCCCA GGCTCCTCAT CTATGGTGCA TCCAGCAGGG CCACTGGCAT CCCAGACAGG   180

TTCAGTGGCA GTGGGTCTGG GACAGACTTC ACTCTCACCA TCAGCAGACT GGAGCCTGAA   240

GATTTTGCAG TGTATTACTG TCAGCTTTAT GGTAACTCAC GTTGGACGTT CGGCCAAGGG   300

```
ACCAAGGTGG AGATCAAA                                                   318

(2) INFORMATION FOR SEQ ID NO:10:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GAGCTCACTC AGTCTCCAGC CACCCTGTCT TTGTCTCCAG GGGAAAGAGC CACCCTCTCC       60

TGCAGGGCCA GTCAGAGTGT TAACAAGTAC TTAGCCTGGT ACCAACAGAA ACCTGGCCAG      120

GCTCCCAGGC TCCTCATCTA TGATGCATCC AACAGGGCCA CTGGCATCCC AGCCAGGTTC      180

AGTGGCAGTG GGTCTGGGAC AGACTTCACT CTCACCATCA GCAACCTAGA GCCTGAAGAT      240

TTTGCAGTTT ATTACTGTCA GCAGCGTAGC GACTGGGTCA CTTTCGGCGG AGGGACCAAG      300

GTGGAGATCA AA                                                         312

(2) INFORMATION FOR SEQ ID NO:11:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GAGCTCACGC AGTCTCCAGG CACCCTGTCT TTGTCTCCAG GGGAAAGAGC CACCCTCTCC       60

TGCGGGCCA GTCAGAGTGT TAGGAGCAAC TACTTAGCCT GGTACCAGCA AAAACCTGGC      120

CAGGCTCCCA GGCTCCTCAT CTATGGTGTA TCCAGCAGGG CCACTGGCAT CCCAGACAGG      180

TTCAGTGGCA GTGGGTCTGG GACAGACTTC ACTCTCACCA TCAGCAGACT GGAGCCTGAA      240

GATTTTGCAG TGTATTACTG TCAGCAGTAT GGTAGCTCAC CTCGGACTTT TGGCCAGGGG      300

ACCAAGTTGG AGATCAAA                                                   318

(2) INFORMATION FOR SEQ ID NO:12:

(i) SEQUENCE CHARACTERISTICS:
        (A) LENGTH: 315 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GAGCTCACGC AGTCTCCAGC CACCCTGTCT GTGTCTCCAG GGGAAAGAGC CTCCCTCTCC       60

TGCAGGGCCA GTCAGAGTGT CGGTAACAAT TTAGCTTGGT ATCAGCAGAA ACCTGGCCAG      120

GCTCCCAGGC TCCTCATTTA TGGTGGAAAC ACCAGAGCCA CTGGTACCCC AGACAGGTTC      180

AGTGGCAGTG GGTCTGGGAC AGAATTCACT CTCACCATCA GCAGCCTGCA GTCTGAGGAC      240

TTTGCAGTTT ATTTCTGTCA ACACTATAGT ACCTGGCCGC TCACTTTCGG CGGGGGGACC      300

AAGGTCGAGT TCAAG                                                      315
```

(2) INFORMATION FOR SEQ ID NO:13:

(i) SEQUENCE CHARACTERISTICS:
        (A) LENGTH: 384 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
CTCGAGCAGT CTGGGGCTGA GGTGAGGAAG CCTGGGTCCT CGGTGAAGGT CTCCTGCAAG      60

GCTTCTGGAG GCACCTTCAG CGGCCATGTT ATCACCTGGG TGCGACAGGC CCCTGGACAA     120

GGACTTGAGT GGATGGGAGA GAGCATCCCT ATCTTTGGTT CCGCAAACTA CGCTCAAAAC     180

TACGCTCAGA AATTCCGGGA CAGAGTCTCG ATTATCGCGG ACGAATCCAC GAGCACGTCG     240

TTCATTGAGC TGAGCAACCT GAGATCTGAC GACACGGCCG TCTACTACTG TGCGAGAGAC     300

CCTCCAAGAT ATTGCAGTGC TGGTAGATGC TACCCGGGAT TCTTCCAGCA GTGGGGCCAG     360

GGCACCCTCG TCACCGTCTC CTCA                                            384
```

(2) INFORMATION FOR SEQ ID NO:14:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
CTCGAGCAGT CTGGGGCTGA GGTGAAGAAG CCTGGGTCCT CGGTGAAGGT CTCCTGTCAG      60

GTTTTTGGAG ACACCTTCAG CAGATACACT ATTCAGTGGT TGCGACAGGC CCCTGGACAA     120

GGGCCTGAGT GGATGGGAAA TATCATCCCT GTCTATAATA CACCAAACTA CGCGCAGAAG     180

TTTCAGGGCA GACTCTCGAT AACCGCCGAC GATTCCACGA GCACAGCCTA CATGGAACTG     240

AGTAGCCTCA GATCTGAGGA CACGGCCGTC TATTTCTGTG CGAGAGTCGT AATACCAAAT     300

GCAATCCGGC ACACGATGGG ATATTACTTT GACTACTGGG GCCAGGGAAC CCTGGTCACC     360

GTCTCCTCA                                                             369
```

(2) INFORMATION FOR SEQ ID NO:15:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
CTCGAGCAGT CTGGGGCTGA GGTGAAGAAG CCTGGGTCCT CAGTGAAGGT CTCCTGCAAG      60

GCTTCTGGAG GCACCTTCAG CGGCCATGTT ATCAGCTGGG TGCGACAGGC CCCTGGACAA     120

GGGCTTGAGT GGATGGGGGG GAGTATCTCT TTCTTTGGCA CATCAAACTC CGCACAGAAG     180

TTCCAGGGCA GAGTCTCGAT TACCGCGGAC GAATCCGCGA GCACAGCCTA CATGGAGCTG     240

AGTAGCCTGA GATCGGAGGA CACGGCCATC TATTACTGTG CGAAAGACCC TCCAAGATTT     300

TGTAGTGGTG GTAACTGCTA CCCGGGGTTC TTCCAGCAGT GGGGCCAGGG CACCCTGGTC     360

ACCGTCTCCT CA                                                         372
```

(2) INFORMATION FOR SEQ ID NO:16:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
CTCGAGTCGG GGGGAGGCGT GGTCCAGCCT GGGAGGTCCC TGAGACTCTC CTGTGCAGCG      60

TCTGGATTCA CCTTCAAGAC GTATGGCATG CACTGGGTCC GCCAGGCTCC AGGCAAGGGG     120

CTGGAGTGGG TGGCAGGTAT TTCGTTTGAT GGAAGTAACC AATATTACGC AGACTCCGTG     180

AAGGGCCGAT TCATCGTCTC CAGAGACAAT TCCAGGACA CGGTGTTTCT GCAGATGAGC      240

AGCCTGAGAC TCGAGGACAC GGCTGTCTAT TACTGTGCGA CAGAGGGTTC TCCTTTTGGC     300

TCGATTAAGG GGCGTTACTA CCTTGAAAAT TGGGGCCAGG GAACCCTGGT CACCGTCTCC     360

TCA                                                                   363
```

(2) INFORMATION FOR SEQ ID NO:17:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
Val Ala Gly Val Asp Ala Ser Thr Tyr Thr Thr Gly Gly Gln Ser Gly
1               5                  10                  15

Arg Thr Thr Tyr Gly Ile Val Gly Leu Phe Ser Leu Gly Pro Ser Gln
            20                  25                  30

Lys Leu Ser Leu Ile Asn Thr Asn Gly Ser Trp His Ile Asn Arg
        35                  40                  45
```

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
CAACGCAATT AATGTGAGTT AG                                              22
```

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
GCCCCCTTAT TAGCGTTTGC CATC                                            24
```

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
ATAGAAGTTG TTCAGCAGGC A                                              21
```

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
GTCGTTGACC AGGCAGCCCA G                                              21
```

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
AAGACAGCTA TCGCGATTGC AG                                             22
```

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
ACCTATTGCC TACGGCAGCC G                                              21
```